United States Patent
Mokhadinyana et al.

(10) Patent No.: US 9,546,117 B2
(45) Date of Patent: Jan. 17, 2017

(54) TETRAMERISATION OF ETHYLENE

(71) Applicant: SASOL TECHNOLOGY (PROPRIETARY) LIMITED, Rosebank (ZA)

(72) Inventors: Molise Stephen Mokhadinyana, Sasolburg (ZA); Munaka Christopher Maumela, Sasolburg (ZA); Moses Mokgolela Mogorosi, Sasolburg (ZA); Matthew James Overett, Johannesburg (ZA); Jan-Albert Van Den Berg, Vanderbijlpark (ZA); Werner Janse Van Rensburg, Gardens (ZA); Kevin Blann, Johannesburg (ZA)

(73) Assignee: Sasol Technology (Proprietary) Limited, Rosebank (ZA)

( * ) Notice: Subject to any disclaimer, the term of this patent is extended or adjusted under 35 U.S.C. 154(b) by 0 days.

(21) Appl. No.: 14/888,712

(22) PCT Filed: May 6, 2014

(86) PCT No.: PCT/IB2014/061237
§ 371 (c)(1),
(2) Date: Nov. 3, 2015

(87) PCT Pub. No.: WO2014/181250
PCT Pub. Date: Nov. 13, 2014

(65) Prior Publication Data
US 2016/0075616 A1    Mar. 17, 2016

(30) Foreign Application Priority Data
May 9, 2013 (ZA) .................................. 2013/03363

(51) Int. Cl.
*C07C 2/36* (2006.01)

(52) U.S. Cl.
CPC ............. *C07C 2/36* (2013.01); *C07C 2531/14* (2013.01); *C07C 2531/24* (2013.01); *C07C 2531/34* (2013.01)

(58) Field of Classification Search
CPC .... C07C 2/36; C07C 2531/14; C07C 2531/24; C07C 2531/34
See application file for complete search history.

(56) References Cited

U.S. PATENT DOCUMENTS

2006/0229480 A1* 10/2006 Blann .................... B01J 31/143
585/535

FOREIGN PATENT DOCUMENTS

| WO | 02/04119 A1 | 1/2002 |
| WO | 2004/056479 A1 | 7/2004 |
| WO | 2008/088178 A1 | 7/2008 |

OTHER PUBLICATIONS

Stennett et al., "N, N-Diphospholylamines—A New Family of Ligands for Highly Active, Chromium-Based, Selective Ethene Oligomerisation Catalysts", CHEMCATCHEM, vol. 5, No. 10, Jun. 21, 2013, pp. 2946-2954.
Van Leeuwen et al., "New processes for the selective production of 1-octene", Coordination Chemistry Reviews, vol. 255, No. 13, Oct. 4, 2010, pp. 1499-1517.

* cited by examiner

*Primary Examiner* — Nathan M Nutter
(74) *Attorney, Agent, or Firm* — Whitham, Curtis & Cook, P.C.

(57) ABSTRACT

A process for the tetramerization of ethylene includes contacting ethylene with a catalyst under ethylene oligomerization conditions. The catalyst comprises a source of chromium, a ligating compound, and an activator. The ligating compound includes a phosphine that forms part of a cyclic structure.

21 Claims, No Drawings

TETRAMERISATION OF ETHYLENE

TECHNICAL FIELD

The invention relates to a process for the tetramerisation of ethylene, the process including contacting ethylene with a catalyst under ethylene oligomerisation conditions, said catalyst comprising a source of chromium and novel ligating compounds.

BACKGROUND OF THE INVENTION

It is known that chromium-based catalyst systems with diphosphine ligands catalyse the selective conversion of ethylene to 1-hexene and/or 1-octene depending on the reaction conditions and choice of ligand structure. In particular, the nature and position of any substituents on the aryl rings connected to the phosphines are crucial influences on the selectivity split between 1-hexene and 1-octene. Of particular interest to industry are catalysts for ethylene tetramerisation, as these catalysts are relatively rare. Octene is a valuable co-monomer for the production of high performance linear low density polyethylenes and elastomers, and few selective on-purpose routes to this chemical are known in industry. By comparison, catalysts for ethylene trimerisation are relatively common, and are used industrially by several companies. By tetramerisation it is meant that at least 30% 1-octene is produced in the process.

Non-limiting examples of selective ethylene tetramerisation catalyst systems include the ubiquitous Cr/bis(phosphino)amine (i.e. 'PNP') systems, particularly of the type $(Ar^1)(Ar^2)PN(R)P(Ar^3)(Ar^4)$, where $Ar^1$ to $Ar^4$ are aryl groups such as phenyl and R is a hydrocarbyl or a heterohydrocarbyl group, beginning with PNP ligands containing no substituents on the phenyl rings bonded to the P-atoms (e.g. as described in WO 2004/056479) and those with m or p-methoxy groups on the phenyl rings (e.g. as described in WO 2004/056480). In addition to this, PNP systems containing o-fluoro groups on the phenyl rings are described in US 2008/0242811 and US 2010/0081777, and PNP systems bearing pendant donor atoms on the nitrogen linker are described in WO 2007/088329. Multi-site PNP ligands are discussed in US 2008/0027188. In addition to the Cr/PNP systems, chromium systems bearing N,N-bidentate ligands (e.g. as described in US 2006/0247399) can be used. PNP ligands with alkylamine or phosphinoamine groups bonded to one of the PNP phosphines (i.e. 'PNPNH' and 'PNPNP' ligands) are described in WO 2009/006979. Finally, carbon bridged diphosphine (i.e. 'PCCP' ligands) are described in WO 2008/088178 and WO 2009/022770.

Related ethylene trimerisation catalysts with high selectivity for 1-hexene can be obtained by using PNP ligands with ortho-methoxy or ortho-alkyl substituents on the phenyl rings bonded to the P-atoms (e.g. as described in WO2002/04119, WO2004/056477 and WO2010/034101).

When carrying out a process for tetramerisation of ethylene, the aim is to choose a catalyst system and adjust process conditions in order to produce the maximum amount of 1-octene, as opposed to trimerisation processes where catalysts and process conditions are adjusted to produce the maximum amount of 1-hexene. 1-Hexene is also typically co-produced in a tetramerisation process. Consequently, new tetramerisation catalyst systems which increase catalyst selectivity to 1-octene while reducing selectivity to co-products are highly desirable. Alternatively, new tetramerisation catalysts which produce similar amounts of 1-octene to catalysts known in the art, but which produce more 1-hexene (i.e. reduced C4 and C10+ oligomers) would also be desirable.

In several investigations of structure-selectivity relationships for tetramerisation ligands, the effect of various patterns of ortho-substitution on the phenyl rings of the $(Ar^1)(Ar^2)PN(R)P(Ar^3)(Ar^4)$ ligand (where $Ar_1$-$Ar^4$ are optionally substituted phenyl groups and R is a hydrocarbyl group) has been studied. For example, the effect of ortho-alkyl groups (Blann et al, Chem. Commun. 2005, 620), ortho-methoxy groups (Overett at all. Chem Commun 2005, 622) and ortho-fluorine groups (US 2010/008177) on selectivity has been reported. These ortho-substitutions may produce significant selectivity benefits in terms of reduced co-products (e.g. C10-C14 secondary products or reduced C6 cyclics). However, in all cases the effect of ortho-substitution is to reduce the 1-octene:1-hexene ratio relative to the equivalent unsubstituted PNP ligand. Consequently, ligand motifs that act to increase the intrinsic 1-octene selectivity and which may be used in combination with a beneficial ortho-substitution motif on the same PNP ligand structure may be particularly beneficial.

The formation of a high molecular weight polymer co-product by the Cr-based ethylene tetramerisation catalyst may present a major technical challenge when commercialising an ethylene tetramerisation process. Polymer fouling of the reactor or downstream sections will reduce plant run time and necessitate shut-downs due to blockages and loss of reaction cooling due to coating of heat exchange surfaces. When running tetramerisation processes at reaction temperatures in the range of 40 to 80° C., as is taught in the art, most of the polymer co-product precipitates in the reactor, which can result in fouling of process equipment. To ensure process reliability and adequate run-times under such reaction conditions, it may be necessary to utilise expensive or energy-intensive process design features.

Running a tetramerisation process at process conditions whereby the polymer co-product remains predominantly dissolved in the liquid reaction medium in the reactor (i.e. a solution phase process) would substantially reduce the possibility of reactor or downstream fouling. In addition, a further benefit of such a process might be that a cheaper or more energy-efficient process design could be used, due to the reduced likelihood of fouling process equipment.

A solution phase process could be achieved by using higher reaction temperatures than typically taught in the art, specifically temperatures of above 80° C. However, the art teaches away from running at higher temperatures due to undesirable effects including poor catalyst activity, increased polymer formation and increased selectivity towards 1-hexene. It is well known in the art of the invention that higher reaction temperatures shift the selectivity from 1-octene towards 1-hexene. New tetramerisation catalysts have been developed that show improved performance at high temperatures, but these modifications reduce the octene:hexene ratio further. In this context, novel tetramerisation catalyst structures that increase the intrinsic selectivity towards 1-octene are highly desirable.

SUMMARY OF THE INVENTION

According to one aspect of the invention there is provided a process for the tetramerisation of ethylene, the process including contacting ethylene with a catalyst under ethylene oligomerisation conditions, said catalyst comprising:
i) a source of chromium;
ii) a ligating compound of the formula

wherein A is selected from the group consisting of nitrogen, phosphorus, and oxygen;

X is a linking group between A and Y;

m is independently 1 or 2;

$R^1$ is a hydrogen, a hydrocarbyl group, an organoheteryl group or a heterohydrocarbyl group with each $R^1$ being the same or being different where m is 2; and Y is an optionally substituted group that can be represented as

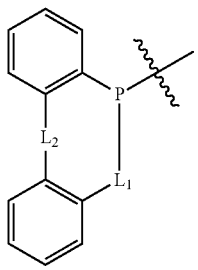

such that P is a phosphorous atom and bonds to X; and $L_1$ and $L_2$ are linkers selected from the group comprising a covalent bond and an optionally substituted single atom bonded to both of the linked carbon or phosphorous atoms; and iii) optionally a catalyst activator or combination of catalyst activators.

According to some embodiments of the invention, there is provided a process for the tetramerisation of ethylene, the process including contacting ethylene with a catalyst under ethylene oligomerisation conditions, said catalyst comprising:

i) a source of chromium;

ii) a ligating compound of the formula $R^1R^2PXY$ wherein P is a phosphorous atom;

X is a linking group between P and Y;

$R^1$ and $R^2$ are independently a hydrocarbyl group, an organoheteryl group or a heterohydrocarbyl group; and Y is an optionally substituted group that can be represented as

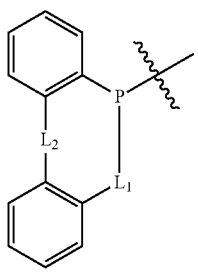

such that P is a phosphorous atom which bonds to X; and $L_1$ and $L_2$ are linkers selected from the group comprising a covalent bond and an optionally substituted single atom bonded to both of the linked carbon or phosphorous atoms; and iii) optionally a catalyst activator or combination of catalyst activators.

DETAILED DESCRIPTION OF EMBODIMENTS OF THE INVENTION

The invention relates to a process for the tetramerisation of ethylene, the process including contacting ethylene with a catalyst under ethylene oligomerisation conditions, said catalyst comprising a source of chromium, a ligating compound, which compound includes one phosphine that forms part of a cyclic structure, and an activator.

In the specification, the following definitions apply:

A "hydrocarbyl group" as per IUPAC includes a univalent group formed by removing one hydrogen atom from a hydrocarbon;

A "heterohydrocarbyl group" as defined herein is a univalent group formed by removing one hydrogen atom from a carbon atom of a heterohydrocarbon, that is a hydrocarbon compound which includes at least one hetero atom (that is, not being H or C), and which group covalently bonds with one other moiety through the resultant free valency on that carbon atom;

An "organoheteryl group" as per IUPAC includes univalent groups containing carbon, which are thus organic, but which have their free valence at an atom other than carbon;

A "hydrocarbylene group" as per IUPAC includes divalent groups formed by removing two hydrogen atoms from a hydrocarbon, the free valencies of which are not engaged in a double bond.

A "heterohydrocarbylene group" as defined herein is a divalent group formed by removing two hydrogen atoms from either one or two carbon atoms of an organic molecule containing at least one heteroatom, the free valencies of which are not engaged in a double bond.

Chromium Source (i):

Any source of chromium that allows the oligomerisation to proceed may be used. The source of chromium may be an inorganic salt, an organic salt, a coordination compound or an organometallic complex.

In some embodiments the source of chromium is selected from the group consisting of chromium trichloride tristetrahydrofuran complex; (benzene)tricarbonyl chromium; chromium (III) octanoate; chromium hexacarbonyl; chromium (III) acetylacetonate; chromium (III) naphthenate; chromium (Ill) 2-ethylhexanoate; chromium (III) acetate, chromium (III) 2,2,6,6-tetramethylheptadionate; and chromium (III) chloride. In some embodiments it is chromium (Ill) acetylacetonate or chromium (III) 2-ethylhexanoate.

The chromium source may be introduced to the process as a coordination complex of the ligating compound. However, for reasons of cost and commercial operability, in some embodiments the ligating compound and chromium source are added as separate components to the process. Catalyst systems which give good catalyst performance only when an isolable chromium-ligand coordination complex is used therefore suffer a disadvantage to catalyst systems which can be prepared by mixing a chromium source and ligand in the process.

Ligating Compound (ii):

Linking Group X

X may be selected from the group consisting of an organic linking group such as a hydrocarbylene, heterohydrocarbylene; an inorganic linking group comprising either a single- or two-atom linker spacer; and a group comprising dimethylmethylene, ethane-1,2-diyl, ethene-1,2-diyl, propane-1,2- diyl, propane-1,3-diyl, cyclopropane-1,1-diyl, cyclopropane-1,2-diyl, butane-2,3-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracenediyl, 1,2-catecholate, 1,2-diarylhydrazine-1,2-diyl (—N(Ar)—N(Ar)— where Ar is an aryl group), 1,2-dialkylhydrazine-1,2-diyl (—N(Alk)-N(Alk)- where Alk is an alkyl or a cycloalkyl group), 1-alkyl-2-arylhydrazine-1,2-diyl (—N(Alk)-N(Ar)— where Alk is an alkyl or a cycloalkyl group and Ar is an aryl group), —N(R')—X$^1$—N(R")— where R' and R" are independently alkyl, cycloalkyl or aryl groups and X$^1$ is a hydrocarbylene group, =C(R')—N(R")— or =C(R')—C(R")(R'")— where = denotes a double bond and R', R" and R'" are independently hydrogen, alkyl, cycloalkyl or aryl groups, —B(R$^5$)—, —Si(R$^5$)$_2$—, —P(R$^5$)— and —N(R$^5$)— where R$^5$ is hydrogen, a hydrocarbyl group, an organoheteryl group or a heterohydrocarbyl group. Preferably R$^5$ is a hydrocarbyl group or a heterohydrocarbyl group.

For the embodiment of the invention where the ligating compound is of the form $(R^1)_mAXY$, X may be bonded to A through either a single covalent bond or a double covalent bond, as required by the valence of the $(R^1)_mA$ moiety. For the case where A is a nitrogen or phosphorous atom, X will be bound to A through a single covalent bond if m is equal to 2, and through a double covalent bond if m is equal to 1.

In some embodiments X consists of —N(R$^6$)—, —N(R$^6$)—N(R$^7$)—, —C(R$^6$)(R$^7$)—N(R$^8$)—, =C(R$^6$)—N(R$^7$)—, or a hydrocarbylene, where R$^6$, R$^7$ and R$^8$ are independently a hydrogen, a hydrocarbyl group, a heterohydrocarbyl group or an organoheteryl group. In some embodiments R$^6$-R$^8$ may be an alkyl, cycloalkyl, substituted alkyl, substituted cycloalkyl, aryl, substituted aryl, aryloxy, substituted aryloxy, alkoxycarbonyl, carbonyloxy, alkoxy, aminocarbonyl, carbonylamino, dialkylamino, pyrolyl, silyl group or derivative thereof, and aryl substituted with any of these substituents. In some embodiments R$^6$-R$^8$ may be an alkyl, cycloalkyl, substituted alkyl, substituted cycloalkyl, aryl, substituted aryl, dialkylamino, silyl group or derivative thereof. In some embodiments, R$^6$-R$^8$ consist of hydrocarbyl groups, such as methyl, ethyl, propyl, allyl, isopropyl, cyclopropyl, butyl, tertiary-butyl, sec-butyl, cyclobutyl, pentyl, isopentyl, 1,2-dimethylpropyl (3-methyl-2-butyl), 1,2,2-trimethylpropyl (R/S-3,3-dimethyl-2-butyl), 1-(1-methylcyclopropyl)-ethyl, neopentyl, cyclopentyl, cyclohexyl, hexyl, cycloheptyl, cyclo-octyl, decyl, cyclodecyl, 1,5-dimethylheptyl, 1-methylheptyl, 2-naphthylethyl, 1-naphthylmethyl, adamantylmethyl, 1-adamantyl, 2-adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, (1,1'-bis(cyclohexyl)-4,4'-methylene), 1,6-hexylene, 1-naphthyl, 2-naphthyl, diphenylmethyl, 1,2-diphenyl-ethyl, phenylethyl, 2-methylphenyl, 3-methylphenyl, 4-methylphenyl, 2,6-dimethyl-phenyl, or a 1,2,3,4-tetrahydronaphthyl.

In a preferred embodiment X is a hydrocarbylene, —N(R$^5$)—, —N(R$^5$)—N(R$^6$)—, =C(R$^7$)—N(R$^5$)—, —N(R$^5$)—C(R$^7$)(R$^6$)—, N(R$^5$)—X$^1$—N(R$^6$) where R$^5$ and R$^6$ are independently a hydrocarbyl group, an organoheteryl group or a heterohydrocarbyl group, R$^7$ and R$^8$ are independently a hydrogen, a hydrocarbyl group, an organoheteryl group or a heterohydrocarbyl group, and X$^1$ is a hydrocarbylene group.

X, in some embodiments, is —N(R$^9$)—, where R$^9$ is a hydrocarbyl group, a heterohydrocarbyl group or an organoheteryl group. In some embodiments R$^9$ is a hydrocarbyl group or a heterohydrocarbyl group. In some embodiments R$^9$ is an alkyl, cycloalkyl or aryl group. In some preferred embodiments R$^9$ is an alkyl or cycloalkyl group. In some embodiments R$^9$ is an alkyl group of the form —CH$_2$R$^{10}$, where R$^{10}$ is hydrogen or an alkyl group or a cycloalkyl group. In some embodiments R$^9$ is methyl or a linear alkyl group.

Nature of the Group $(R^1)_mA$, for the Embodiment of the Invention where the Ligating Compound is of the Form $(R^1)_mAXY$ For the embodiment of the invention where the ligating compound is of the form $(R^1)_mAXY$, A is selected from the group consisting of nitrogen, phosphorus, and oxygen. In some embodiments, A is selected from the group consisting of nitrogen and phosphorous. In some embodiments, A is selected from the group consisting of nitrogen and phosphorous and is bonded to X through a single covalent bond, in which case m is equal to 2. In another embodiment, A is a nitrogen atom and is bonded to X through a double covalent bond, in which case m is equal to 1.

For the embodiment of the invention where the ligating compound is of the form $(R^1)_mAX$, R$^1$ is a hydrogen, a hydrocarbyl group, an organoheteryl group or a heterohydrocarbyl group with each R$^1$ being the same or being different where m is equal to 2. In some embodiments, R$^1$ is a hydrocarbyl, an organoheteryl group or a heterohydrocarbyl group. In some embodiments, R$^1$ is a hydrocarbyl or heterohydrocarbyl group. In some embodiments, R$^1$ is an aromatic, including a heteroaromatic, group directly bonded to A. In some embodiments, R$^1$ is an optionally substituted phenyl group. In some embodiments, R$^1$ is selected from a group consisting of phenyl, 2-methylphenyl, 2-fluorophenyl, 2-methoxyphenyl, 2-trifluoromethoxyphenyl, and 1-benzofuran-7-yl.

Nature of the Groups R$^1$ and R$^2$, for the Embodiment of the Invention where the Ligating Compound is of the Form R$^1$R$^2$PXY R$^1$ and R$^2$ are independently a hydrocarbyl, an organoheteryl group or a heterohydrocarbyl group. In some embodiments, R$^1$ and R$^2$ are independently hydrocarbyl or heterohydrocarbyl groups. In some embodiments, both R$^1$ and R$^2$ are aromatic, including heteroaromatic, groups directly bonded to P. In some embodiments, both R$^1$ and R$^2$ are optionally substituted phenyl groups. In some embodiments, R$^1$ and R$^2$ may independently be selected from a group consisting of phenyl, 2-methylphenyl, 2-fluorophenyl, 2-methoxyphenyl, 2-trifluoromethoxyphenyl, and 1-benzofuran-7-yl.

Nature of the Group Y

Y is an optionally substituted group that can be represented as

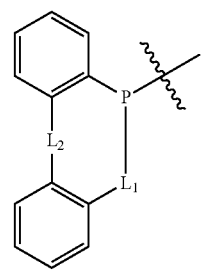

such that P is a phosphorous atom and bonds to X; and
L$_1$ and L$_2$ are linkers selected from the group comprising
a covalent bond and an optionally substituted single atom bonded to both of the linked carbon or phosphorous atoms.

In some embodiments, $L_1$ and $L_2$ may be selected from the group comprising a covalent bond, a heteroatom, a substituted heteroatom, —C(=O)—, —CR³R⁴—, where R³ and R⁴ are independently a hydrogen, a hydrocarbyl group, a heterohydrocarbyl group or an organoheteryl group.

In some embodiments, $L_1$ and $L_2$ can be selected from the group comprising a covalent bond, —O—, —S—, —NR₃—, —P(=O)R³—, P(=Se)R³—, P(=S)R³—, —SiR³R⁴—, —CR³R⁴—, —C(=O)— where R³ and R⁴ are independently a hydrogen, a hydrocarbyl group, a heterohydrocarbyl group or an organoheteryl group.

In some embodiments, $L_1$ and $L_2$ can be selected from the group comprising a covalent bond, —O—, —S—, —NR₃—, —SiR³R⁴—, —CR³R⁴—, —C(=O)— where R³ and R⁴ are independently a hydrogen, a hydrocarbyl group, a heterohydrocarbyl group or an organoheteryl group.

In some embodiments, $L_1$ and $L_2$ can be selected from the group comprising a covalent bond, —O—, —S—, —NR₃—, where R³ is a hydrogen, a hydrocarbyl group, a heterohydrocarbyl group or an organoheteryl group.

In some embodiments, $L_1$ and $L_2$ are either a covalent bond or —O—.

In some embodiments, at least one of $L_1$ and $L_2$ is a covalent bond.

In some embodiments, either $L_1$ and $L_2$ are covalent bonds; or $L_1$ is —O— and $L_2$ is a covalent bond; or $L_1$ is a covalent bond and $L_2$ is —O—.

In some embodiments, both of $L_1$ and $L_2$ are covalent bonds. In this case, Y (which is formally named dibenzophosphol-5-yl or 5H-benzo[b]phosphoindole) has the following structure:

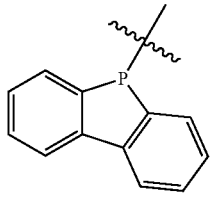 [SMILES: *p1c2ccccc2c2ccccc21]

In some embodiments, $L_1$ is —O— and $L_2$ is a covalent bond. In this case, Y (which is formally named 9-oxa-10-phosphaphenanthren-10-yl or 6H-dibenzo[c,e][1,2]oxaphosphirine) has the following structure:

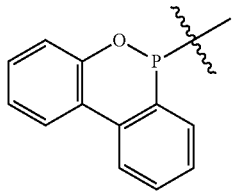 [SMILES: *P1Oc2ccccc2-c2ccccc21]

In some embodiments, $L_1$ is a covalent bond and $L_2$ is —O—. In this case, Y (which is formally named phenoxaphosphin-10-yl or 10H-phenoxaphosphine) has the following structure:

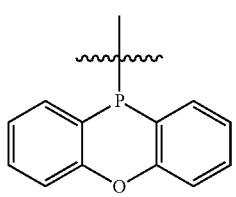 [SMILES: *P1c2ccccc2Oc2ccccc21]

Y may optionally be substituted at one or more of the aromatic ring positions with groups other than hydrogen. In some embodiments, the substituents may be hydrocarbyl groups, heterohydrocarbyl or organoheteryl groups or halogen atom substituents. In some embodiments, Y is not substituted, with all ring positions other than those bonded to P, $L_1$ and $L_2$ being bonded to hydrogen atoms.

Other Considerations

For the embodiment of the invention where the ligating compound is of the form R¹R²PXY, R¹ and R² may independently be linked to each other, or to X, to form a cyclic structure.

For the embodiment of the invention where the ligating compound is of the form R¹R²PXY, the ligating compound may also include multiple R¹R²P¹XY units. Non-limiting examples of such ligands include dendrimeric ligands as well as ligands where the individual units are coupled, for example via the linking group X.

It will be appreciated that a diphosphinoimine compound of the form R¹R²P¹—P²(=NR⁹)R³R⁴ ('P—P=N') is a rearranged isomer of the diphosphinoamine compound R¹R²P¹N(R⁹)P²R³R⁴ ('P—N—P') as shown by Dyson et al in Inorganica Chimica Acta 359 (2006) 2635-2643. Similarly, it may be possible that a ligating compound of the form R¹R²PXY, where Y is defined as in the current invention and where X is —N(R⁹)—, exists in its isomeric 'P—P=N' form.

Regardless of the structural formulation of the ligating compound in its pure and isolated form, its use will fall under the present invention if it exists in the 'P—N—P' form when used in a tetramerisation process.

In some embodiments the ligating compound may be one of:

(Dibenzophosphol-5-yl)N(n-butyl)P(phenyl)₂;
(Dibenzophosphol-5-yl)N(n-butyl)P(2-methylphenyl)₂;
(Dibenzophosphol-5-yl)N(i-propyl)P(phenyl)₂;
(Dibenzophosphol-5-yl)N(i-propyl)P(2-methylphenyl)₂;
(Dibenzophosphol-5-yl)N(i-propyl)P(2-methylphenyl)(phenyl);
(Dibenzophosphol-5-yl)N(i-propyl)P(2-ethylphenyl)(phenyl);
(Dibenzophosphol-5-yl)N(n-butyl)P(1-benzofuran-7-yl)(phenyl);
(Dibenzophosphol-5-yl)N(n-butyl)P(1-benzofuran-7-yl)₂;
(Dibenzophosphol-5-yl)N(n-butyl)P(2-methoxyphenyl)₂;
(Dibenzophosphol-5-yl)N(n-butyl)P(2-methoxyphenyl)(phenyl);
(Dibenzophosphol-5-yl)N(n-butyl)P(2-fluorophenyl)₂;
(Dibenzophosphol-5-yl)N(n-butyl)P(2-fluorophenyl)(phenyl);
(Dibenzophosphol-5-yl)N(i-propyl)P(2-fluorophenyl)₂;
(Dibenzophosphol-5-yl)N(i-propyl)P(2-fluorophenyl)(phenyl);
(Dibenzophosphol-5-yl)N(Me)N(Me)P(phenyl)₂;
(Dibenzophosphol-5-yl)N(Me)N(Me)P(2-methylphenyl)₂;
(Dibenzophosphol-5-yl)N(i-propyl)P(2-trifluoromethoxyphenyl)₂;
(Dibenzophosphol-5-yl)N(i-propyl)P(2-trifluoromethoxyphenyl)(phenyl);
(Dibenzophosphol-5-yl)N(Me)N(n-butyl)P(phenyl)₂;
(Dibenzophosphol-5-yl)N(n-butyl)N(Me)P(phenyl)₂;
(Dibenzophosphol-5-yl)-1,2-phenylene-P(phenyl)₂;
(Dibenzophosphol-5-yl)-1,2-phenylene-P(2-fluorophenyl)(phenyl);
(Dibenzophosphol-5-yl)-1,2-phenylene-P(2-fluorophenyl)₂;
(Dibenzophosphol-5-yl)-1,2-phenylene-P(2-methylphenyl)₂;
(Dibenzophosphol-5-yl)CH₂N(naphthyl)P(phenyl)₂;
(Dibenzophosphol-5-yl)N(naphthyl)CH₂P(phenyl)₂;
(Dibenzophosphol-5-yl)CH₂N(naphthyl)P(2-fluorophenyl)₂;

(Dibenzophosphol-5-yl)N(naphthyl)CH$_2$P(2-methylphenyl)$_2$;
(Dibenzophosphol-5-yl)N(Me)CH$_2$CH$_2$CH$_2$CH$_2$N(Me)P(phenyl)$_2$;
(Dibenzophosphol-5-yl)N(Me)CH$_2$CH$_2$CH$_2$CH$_2$N(Me)P(2-fluorophenyl)$_2$;
(Dibenzophosphol-5-yl)N(H)C(benzyl)=N(2,6-dimethylphenyl);
(Dibenzophosphol-5-yl)N(H)C(phenyl)=N(2,6-dimethylphenyl);
(Dibenzophosphol-5-yl)N(H)C(i-propyl)=N(2,6-dimethylphenyl);
(Dibenzophosphol-5-yl)N(methyl)C(benzyl)=N(2,6-dimethylphenyl);
(Dibenzophosphol-5-yl)N(H)C(benzyl)=N(phenyl);
(Dibenzophosphol-5-yl)N(H)C(4-methylbenzyl)=N(2,6-dimethylphenyl);
(Dibenzophosphol-5-yl)N(H)C(4-methylbenzyl)=N (phenyl);
(Phenoxaphosphin-10-yl)N(n-butyl)P(phenyl)$_2$;
(Phenoxaphosphin-10-yl) N(n-butyl)P(2-methylphenyl)$_2$;
(Phenoxaphosphin-10-yl)N(i-propyl)P(phenyl)$_2$;
(Phenoxaphosphin-10-yl)N(i-propyl)P(2-methylphenyl)$_2$;
(Phenoxaphosphin-10-yl)N(i-propyl)P(2-methylphenyl)(phenyl);
(Phenoxaphosphin-10-yl)N(i-propyl)P(2-ethylphenyl)(phenyl);
(Phenoxaphosphin-10-yl)N(n-butyl)P(1-benzofuran-7-yl)(phenyl);
(Phenoxaphosphin-10-yl)N(n-butyl)P(1-benzofuran-7-yl)$_2$;
(Phenoxaphosphin-10-yl)N(n-butyl)P(2-methoxyphenyl)$_2$;
(Phenoxaphosphin-10-yl)N(n-butyl)P(2-methoxyphenyl)(phenyl);
(Phenoxaphosphin-10-yl)N(n-butyl)P(2-fluorophenyl)$_2$;
(Phenoxaphosphin-10-yl)N(n-butyl)P(2-fluorophenyl)(phenyl);
(Phenoxaphosphin-10-yl)N(i-propyl)P(2-fluorophenyl)$_2$;
(Phenoxaphosphin-10-yl)N(i-propyl)P(2-fluorophenyl)(phenyl);
(Phenoxaphosphin-10-yl)N(Me)N(Me)P(phenyl)$_2$;
(Phenoxaphosphin-10-yl)N(Me)N(Me)P(2-methylphenyl)$_2$;
(Phenoxaphosphin-10-yl)N(Me)N(n-butyl)P(phenyl)$_2$;
(Phenoxaphosphin-10-yl)N(n-butyl)N(Me)P(phenyl)$_2$;
(Phenoxaphosphin-10-yl)-1,2-phenylene-P(phenyl)$_2$;
(Phenoxaphosphin-10-yl)-1,2-phenylene-P(2-fluorophenyl)(phenyl);
(Phenoxaphosphin-10-yl)-1,2-phenylene-P(2-fluorophenyl)$_2$;
(Phenoxaphosphin-10-yl)-1,2-phenylene-P(2-methylphenyl)$_2$;
(Phenoxaphosphin-10-yl)CH$_2$N(naphthyl)P(phenyl)$_2$;
(Phenoxaphosphin-10-yl)N(naphthyl)CH$_2$P(phenyl)$_2$;
(Phenoxaphosphin-10-yl)CH$_2$N(naphthyl)P(2-fluorophenyl)$_2$;
(Phenoxaphosphin-10-yl)N(naphthyl)CH$_2$P(2-methylphenyl)$_2$;
(Phenoxaphosphin-10-yl)N(Me)CH$_2$CH$_2$CH$_2$CH$_2$N(Me)P(phenyl)$_2$;
(Phenoxaphosphin-10-yl)N(Me)CH$_2$CH$_2$CH$_2$CH$_2$N(Me)P(2-fluorophenyl)$_2$;
(9-oxa-10-phospha-phenanthren-10-yl)N(n-butyl)P(phenyl)$_2$;
(9-oxa-10-phospha-phenanthren-10-yl)N(n-butyl)P(2-methylphenyl)$_2$;
(9-oxa-10-phospha-phenanthren-10-yl)N(i-propyl)P(phenyl)$_2$;
(9-oxa-10-phospha-phenanthren-10-yl)N(i-propyl)P(2-methylphenyl)$_2$;
(9-oxa-10-phospha-phenanthren-10-yl)N(i-propyl)P(2-methylphenyl)(phenyl);
(9-oxa-10-phospha-phenanthren-10-yl)N(i-propyl)P(2-ethylphenyl)(phenyl);
(9-oxa-10-phospha-phenanthren-10-yl)N(n-butyl)P(1-benzofuran-7-yl)(phenyl);
(9-oxa-10-phospha-phenanthren-10-yl)N(n-butyl)P(1-benzofuran-7-yl)$_2$;
(9-oxa-10-phospha-phenanthren-10-yl)N(n-butyl)P(2-methoxyphenyl)$_2$;
(9-oxa-10-phospha-phenanthren-10-yl-N(n-butyl)P(2-methoxyphenyl)(phenyl);
(9-oxa-10-phospha-phenanthren-10-yl)N(n-butyl)P(2-fluorophenyl)$_2$;
(9-oxa-10-phospha-phenanthren-10-yl)N(n-butyl)P(2-fluorophenyl)(phenyl);
(9-oxa-10-phospha-phenanthren-10-yl)N(i-propyl)P(2-fluorophenyl)$_2$;
(9-oxa-10-phospha-phenanthren-10-yl)N(i-propyl)P(2-fluorophenyl)(phenyl);
(9-oxa-10-phospha-phenanthren-10-yl)N(Me)N(Me)P(phenyl)$_2$;
(9-oxa-10-phospha-phenanthren-10-yl)N(Me)N(Me)P(2-methylphenyl)$_2$;
(9-oxa-10-phospha-phenanthren-10-yl)N(Me)N(n-butyl)P(phenyl)$_2$;
(9-oxa-10-phospha-phenanthren-10-yl)N(n-butyl)N(Me)P(phenyl)$_2$;
(9-oxa-10-phospha-phenanthren-10-yl)-1,2-phenylene-P(phenyl)$_2$;
(9-oxa-10-phospha-phenanthren-10-yl)-1,2-phenylene-P(2-fluorophenyl)(phenyl);
(9-oxa-10-phospha-phenanthren-10-yl)-1,2-phenylene-P(2-fluorophenyl)$_2$;
(9-oxa-10-phospha-phenanthren-10-yl)-1,2-phenylene-P(2-methylphenyl)$_2$;
(9-oxa-10-phospha-phenanthren-10-yl)CH$_2$N(naphthyl)(phenyl)$_2$;
(9-oxa-10-phospha-phenanthren-10-yl)N(naphthyl)CH$_2$P(phenyl)$_2$;
(9-oxa-10-phospha-phenanthren-10-yl)CH$_2$N(naphthyl)P(2-fluorophenyl)$_2$;
(9-oxa-10-phospha-phenanthren-10-yl)N(naphthyl)CH$_2$P(2-methylphenyl)$_2$;
(9-oxa-10-phospha-phenanthren-10-yl)N(Me)CH$_2$CH$_2$CH$_2$CH$_2$N(Me)P(phenyl)$_2$; and
(9-oxa-10-phospha-phenanthren-10-yl)N(Me)CH$_2$CH$_2$CH$_2$CH$_2$N(Me)P (2-fluorophenyl)$_2$.

Activator/Additives (iii):

The above process may include an activator to activate the catalyst. Such an activator is a compound that generates an active catalyst when the activator is combined with the catalyst. These activators may be the same or similar to those found to be useful for activating transition-metal-based olefin polymerisation catalysts, a review of which is provided by Marks [Chem Rev. 2000, 100, 1391-1394]. Mixtures of activators may also be used.

Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminum compounds include compounds of the formula AlR$_3$, where each R is independently C$_1$-C$_{12}$ alkyl, oxygen or halide, and compounds such as LiAlH$_4$ and the like. Examples include trimethylaluminum (TMA), triethylaluminum (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichioride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available aluminoxanes are generally believed to be mixtures of linear and cyclic compounds. The cyclic aluminoxanes can be represented by the formula $[R^{11}AlO]_s$ and the linear aluminoxanes by the formula $R^{12}(R^{13}AlO)_s$ wherein s is a number from about 2 to 50, and wherein $R^{11}$, $R^{12}$, and $R^{13}$ represent hydrocarbyl groups, typically $C_1$ to $C_8$ alkyl groups, for example methyl, ethyl or butyl groups. Alkylaluminoxanes especially methylaluminoxane (MAO) are particularly suitable. (MAO is also referred to as methalumoxane and methylalumoxane in the literature).

It will be recognized by those skilled in the art that commercially available alkylaluminoxanes may contain a proportion of trialkylaluminium. For instance, commercial MAO usually contains approximately 10 wt % trimethylaluminium (TMA), and commercial "modified MAO" (or "MMAO") contains both TMA and TIBA. Quantities of alkylaluminoxane are generally quoted herein on a molar basis of aluminium (and include such "free" trialkylaluminium). The alkylaluminoxane and/or alkylaluminium may be added to the reaction media (i.e. ethylene and/or diluent and/or solvent) prior to the addition of the catalyst or at the same time as the catalyst is added. Such techniques are known in the art of oligomerization and are disclosed in more detail in for example, U.S. Pat. Nos. 5,491,272; 5,750,817; 5,856,257; 5,910,619; and 5,919,996 as well as WO 2008/146215 and WO 2007/007272.

In the preparation of the catalyst systems used in the present invention, the optimal quantity of activating compound to be employed is easily determined by simple testing, for example, by the preparation of small test samples which can be used to oligomerize small quantities of ethylene and thus to determine the activity of the produced catalyst. It is generally found for alkylaluminium and aluminoxane based activators or co-activators that a suitable quantity employed is 0.5 to 2000 moles of aluminium per mole of chromium.

Examples of suitable organoboron activator compounds are boroxines, trimethylboron, triethylboron, triphenylboron, dimethylphenylammoniumtetra(phenyl)borate, trityltetra(phenyl)borate, dimethylphenylammonium tetrakis(pentafluorophenyl)borate, trityl tetrakis(pentafluorophenyl) borate, tris(pentafluorophenyl) boron, sodium tetrakis[(bis-3,5-trifluoromethyl)phenyl]borate, dimethylphenylammonium tetrakis[(bis-3,5-trifluoromethyl)phenyl]borate, and trityl tetrakis[(bis-3,5-trifluoromethyl)phenyl]borate.

Those skilled in the art will recognise that boron-containing activators are commonly used in combination with aluminium alkyl activators.

In some embodiments organoboron activators, as described in WO 2010/092554, include a cation and a non-coordinating anion of the general formula

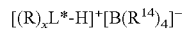

wherein:
L* is an atom selected from the group consisting of N, S and P;

the cation $[(R)_xL^*-H]^+$ is a Bronsted acid;
x is an integer 1, 2 or 3;
each R is the same or different and each is a —H, hydrocarbyl group or a heterohydrocarbyl group;
provided that at least one of R comprises at least 6 carbon atoms and provided further that the total number of carbon atoms in $(R)_x$ collectively is greater than 12;
$R^{14}$ independently at each occurrence is selected from the group consisting of hydride, dialkylamido, halide, alkoxide, aryloxide, hydrocarbyl, halosubstituted-hydrocarbyl radicals, halosubstituted-alkoxide, halosubstituted-aryloxide and a halosubstituted aromatic moiety with at least one halide substituent on the aromatic moiety.

Illustrative, but non-limiting examples of these organoboron activators include methyldi(octadecyl)ammonium tetrakis(pentafluorophenyl) borate and trioctylammonium tetrakis(pentafluorophenyl) borate.

The source of chromium and the organoboron activator may be combined in proportions to provide organoboron compound/chromium molar ratios from about 0.1 to 50 organoboron to 1 chromium, or from about 0.8 to 20 organoboron to 1 chromium, or from 1 to 10 organoboron to 1 chromium.

In some embodiments activators, as described in WO 2007/039851, include a cation and an anion component, and may be represented by the following formula:

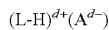

where L is a neutral Lewis base; H is hydrogen; $(L-H)^{d+}$ is a Bronsted acid; $A^{d-}$ is a non-coordinating anion having the charge d−; and d is an integer from 1 to 3.

In these activator compounds, $A^{d-}$ can be a fluorinated aluminate group. Illustrative but non-limiting examples of the anion component $A^{d-}$ are $[Al\{OC(CF_3)_3\}_4]^-$; $[Al(OC_6F_5)_4]^-$; $[Al(C_6F_4O_2)_2]^-$; $[AlF\{OC(CF_3)_3\}_3]^-$; $[Al_2F\{OC(CF_3)_3\}_6]^-$; and $[Ta(OC_6F_5)_6]^-$.

The activator compound may optionally be a solid material, or be supported on an insoluble solid material. For example, aluminoxanes such as MAO and borate activators may be supported on inorganic oxides such as alumina, silica, $MgCl_2$ or the like.

The process may further include the use of compounds that may act as a reducing or oxidising agent, such as sodium or zinc metal and the like, or an oxygen-containing compound, for example oxygen and the like. Additionally, hydrogen ($H_2$) and/or silanes and the like may be used in the catalytic composition or otherwise added to the process. The process may also include the use of a zinc species as an additive, as described in WO 2011/048527, which is herein incorporated by reference. Preferred zinc species would be dialkyl zinc reagents such as dimethylzinc or diethylzinc.

Catalyst Preparation:

The chromium (i) and ligand (ii) may be present in any molar ratio which produces oligomer, and in some embodiments is between 100:1 and 1:100, or from 10:1 to 1:10, or from 3:1 to 1:3. Generally the amounts of (i) and (ii) are approximately equal, i.e. a ratio of between 1.5:1 and 1:1.5.

The ligand, chromium and activators of the catalyst system utilized in the present invention may be added together simultaneously or sequentially, in any order, and in the presence or absence of ethylene in any suitable solvent at any suitable concentration, so as to give an active catalyst. For example, the ligand, chromium, activators and ethylene may be contacted together simultaneously; or the ligand, chromium and activators may be added together simultaneously or sequentially in any order and then contacted with ethylene; or chromium and the ligand may be added together to form an isolable metal-ligand complex and then added to the activator and contacted with ethylene; or the ligand, chromium and activators/co-activators may be added together to form an isolable metal-ligand complex and then contacted with ethylene.

Any or all of the chromium source, ligating compound and activator components utilized in the present invention can be unsupported or supported on a support material, for example silica, alumina, $MgCl_2$ or zirconia, or on a polymer, for example polyethylene, polypropylene, polystyrene or poly(aminostyrene).

Diluent:

The process of the present invention may be carried out in the presence or absence of an added diluent. In some embodiments of the invention the diluents include oligomerisation products e.g. 1-octene and/or 1-hexene, aliphatic and aromatic hydrocarbon solvents and halogenated-aromatic solvents such as chlorobenzene, dichlorobenzene, fluorobenzene and the like. In some embodiments the diluents are aliphatic hydrocarbon solvents including but not limited to Isopar™, iso-octane, cyclohexane, cyclopentane, methylcyclohexane, propane, isobutane, isopentane, neopentane, 2-methylpentane, or 3-methylpentane.

Alternatively the process can be conducted as a bulk process in which essentially neat reactant and/or product olefins serve as the dominant medium.

Process Conditions:

The oligomerisation reaction may take place at any suitable temperature to allow oligomerisation to proceed. Suitable temperatures may be from 0° C. to 200° C. Preferred temperatures are dependent on the process conditions utilized.

In one embodiment, the oligomerisation is conducted under slurry phase conditions, which is herein taken to mean that a substantial portion of any polymer co-product is present in the solid phase, and not predominantly dissolved in the liquid reaction medium under the chosen reaction conditions. Suitable temperatures to achieve this range from 0° C. to about 80° C. Such process conditions may be chosen for optimal catalyst activity and selectivity.

In another embodiment, the oligomerisation is conducted under solution phase conditions, which is herein taken to mean that any polymer co-product remains substantially dissolved in the liquid reaction medium under the chosen reaction conditions. Suitable temperatures to achieve this range from above 80° C. to about 130° C. In some embodiments the temperature range is between 85° C. and 130° C., whilst in other embodiments the temperature range is between 90° C. and 110° C. Such process conditions may be chosen to reduce fouling of the reactor or other process equipment.

Suitable reaction pressures are from atmospheric to 800 atmospheres (bar), or from 5 atmospheres to 100 atmospheres, or from 40 to 100 atmospheres, or from 60 to 100 atmospheres.

There exist a number of options for the tetramerisation reactor including batch, semi-batch, and continuous operation. In some embodiments the process is a continuous process, in which case reactors utilizing both CSTR and plug flow behavior may be considered. There are different potential configurations as a subset of these two types of reactors. For example, CSTR type reactors include bubble columns, stirred tanks, loop reactors with single or two phases while plug flow reactors include fixed bed and homogeneous tubular types of varying residence times. As a further subset, reactors can be configured with different cooling options such as internal or external heat exchangers, interstage coolers, and cold feed heat removal amongst others. All configurations can be run in continuous or batch mode, and there is opportunity to configure the same reactor several times in series or use combinations of different reactor types and cooling techniques together to achieve the desired result.

For systems where tetramerisation takes place in the liquid phase, different mass transfer opportunities exist including jet loop mixing, bubble column sparging, tubular reactor multiple injections and pre-saturation of the feed material amongst others.

The reactor type selected may depend on factors such as heat removal, mechanical robustness with regard to fouling, residence time distributions, product composition effects as a result of secondary reactions and mechanical equipment cost implications. In a slurry phase process where polymer precipitates out of the reaction medium, the selection criteria of heat removal and mechanical robustness with regard to fouling may be expected to dominate and many reactor configurations may therefore be excluded. In a solution phase process, a wider range of reactor configurations may be considered and implemented to optimize factors such as residence time distributions, product composition effects as a result of secondary reactions and mechanical equipment cost implications. In particular, the use of reactors wherein reaction cooling is effected by means of heat exchangers in contact with the reaction medium may be practical in a solution phase process, whereas the susceptibility of such heat exchangers to fouling may rule out such options for a slurry-phase process.

EXAMPLES

The following abbreviations are used in the examples:
PCl chlorophosphine, i.e. $R^1R^2PCl$, where $R^1$ and $R^2$ are hydrocarbyl groups or heterohydrocarbyl groups
n-butyl normal butyl
n-hexyl normal hexyl
i-propyl iso-propyl
Et ethyl
$NEt_3$ Triethylamine
RT room temperature (in the order of 20 to 25° C.)
iPrMgBr.LiCl iso-propyl magnesium bromide lithium chloride
Ph phenyl
PNH phosphinoamine, e.g. $Ar_2PN(R)H$, where Ar is an aryl, and R is a hydrocarbyl group
PNP bis phosphinoamine, e.g. $Ar_2PN(R)PAr_2$, where Ar is an aryl, and R is a hydrocarbyl group
$Et_2O$ diethyl ether
DCM dichloromethane
THF tetrahydrofuran
DMF dimethylformamide
TMP 2,2,4-trimethylpentane
MMAO An aluminoxane product
General Experimental Conditions for Ligand Synthesis All reactions were carried out under an argon atmosphere using a dual vacuum/nitrogen line and standard Schlenk techniques. Solvents were purified via an M-Braun solvent purification system. All reagents purchased from commercial suppliers were used without further purification. NMR spectra were recorded on a Varian 400 MHz spectrometer using CDCl₃. PNP compounds below were prepared by modification of the procedure described in *Synthesis,* 2007, 24, 3863.

Preparation of 5-chlorodibenzophosphole

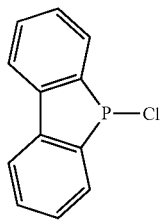 [SMILES: Clp1c2ccccc2c2ccccc21]

To a cooled (0° C.) solution of 2,2'-dibromobiphenyl (4 g, 12.8 mmol) in Et₂O (40 ml), n-butyl lithium (11.3 ml, 28.2 mmol, 2.5 M solution in Et₂O) was added drop-wise. After complete addition the cooling bath was removed and the yellow solution was stirred at room temperature for 1 h. The solution was then frozen with liquid nitrogen (−196° C.). Subsequently, PCl₃ (6.7 ml, 76.9 mmol) was added and the reaction mixture allowed to warm to −110° C. When the reaction mixture began to thaw, it was quickly homogenized with swilling. The homogenous solution was allowed to warm to room temperature with stirring and a white precipitate formed. The reaction mixture was evaporated to dryness, and the residue re-dissolved in Et₂O and filtered through a celite bed to give the product. ³¹P NMR (CDCl₃): δ 68.341 (br. s).

Preparation of (2-methoxyphenyl)₂phosphine chloride

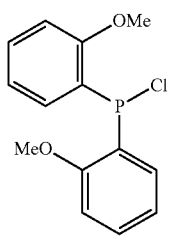

1-Bromo-2-methoxybenzene (1.3 ml, 10.7 mmol) was added to a mixture of magnesium turnings (0.3 g, 12.8 mmol) in anhydrous THF (20 ml). A vigorous reaction ensued. Stirring was continued at room temperature until all the magnesium had dissolved. Once the reaction exotherm had dissipated, the reaction mixture was used for the next step.

The Grignard reagent (separated from excess Mg) was incrementally added to a solution of PCl₃ (0.4 ml, 5.3 mmol) in anhydrous THF (30 ml) at −78° C. After addition was complete, the suspension was stirred at room temperature for a further 15 min after which the reaction was complete as judged by ³¹P NMR. The product was used in the next step without isolation. ³¹P NMR (CDCl₃): δ 69.89 and 63.06 (2×s, corresponding to P—Cl and P—Br).

Preparation of (2-fluorophenyl)₂phosphine chloride

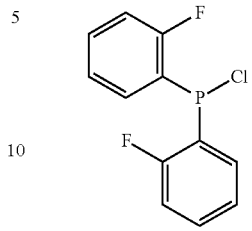

To a cooled (0° C.) solution of 1-bromo-2-fluorobenzene (2.5 ml, 22.9 mmol) in THF (20 ml), iPrMgBr.LiCl (21 ml, 27.5 mmol, 1.3 M solution THF) was added dropwise. After complete addition the cooling bath was removed and the grey solution was stirred at room temperature for 1 h. The solution was subsequently added dropwise to a chilled solution of PCl₃ (1 ml, 11.5 mmol) in THF (−78° C.) and the reaction allowed to stir for a period of 10 min. The homogenous solution was then allowed to warm to room temperature. The reaction mixture was evaporated to dryness, and the residue was re-dissolved in Et₂O and filtered through a celite bed to give the product, which was used in the next step without isolation. ³¹P NMR (CDCl₃): δ 60.29 (t. 1P, J=65.97 Hz).

Preparation of (2-methylphenyl)₂phosphine chloride

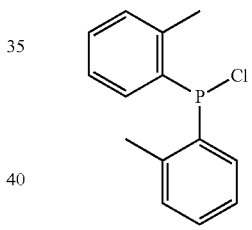

1-Bromotoluene (1.3 mL, 10.7 mmol) was added to a mixture of magnesium turnings (0.3 g, 12.8 mmol) in anhydrous THF (20 ml). A vigorous reaction ensued. Once the reaction exotherm had dissipated, the reaction mixture was used for the next step.

The Grignard reagent (separated from excess Mg) was incrementally added to a solution of PCl₃ (0.4 mL, 5.3 mmol) in anhydrous THF (30 ml) at −78° C. After addition was complete, the suspension was stirred at room temperature for a further 15 min after which the reaction was complete as judged by ³¹P NMR. The product was used in the next step without isolation. ³¹P NMR (CDCl₃): δ 73.1 (s)

Preparation of 7-bromobenzofuran

7-bromobenzofuran was prepared as described in Heterocycl. Commun., Vol. 16(4-6), pp. 249-252, 2010 by Klenk. J. et. al.

Preparation of 1-benzofuran-7-yl magnesium bromide

To magnesium turnings (450 mg, 18.8 mmol) in THF (5 mL) was added 1 iodine crystal and a few drops of 7-bromobenzofuran. A vigorous reaction ensued. The remaining 7-bromo-benzofuran (3.6 g, 18.4 mmol) in THF (10 ml) was added dropwise. The reaction mixture was left to reflux by itself. Once the reaction exotherm had dissipated, the reaction mixture was heated under reflux for about 15 minutes to yield the required Grignard reagent.

Preparation of (1-benzofuran-7-yl)(phenyl)phosphine chloride

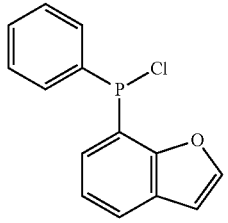 [SMILES: ClP(c1ccccc1)c1cccc2ccoc12]

The Grignard reagent benzofuryl magnesium bromide (prepared as described above) (10.8 mmol) was slowly added to a pre-cooled solution of PhPCl$_2$ (1.5 ml, 10.8 mmol) in anhydrous THF (20 ml) at RT. After addition was complete, the suspension was stirred at room temperature for a further 1 h after which the reaction was complete as judged by $^{31}$P NMR. The product was used in the next step without isolation. $^{31}$P NMR δ 79.4 (s), 67.0 (s).

Preparation of 10-chloro-9-oxa-10-phosphaphenanthrene

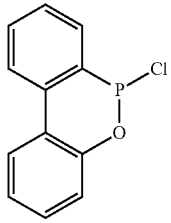

A mixture of PCl$_3$ (20 mL, 31.5 g, 0.23 mol) and 2-phenylphenol (31.2 g, 0.18 mol) was heated gradually to 150° C. over a period of 5 hour with continuous stirring. A slow sweep of nitrogen was maintained to facilitate the ready removal of evolved hydrogen chloride. The reaction mixture was cooled to 25° C., followed by the addition of 0.20 g of anhydrous ZnCl$_2$. The temperature of the reaction mixture was increased to 160° C. over a period of 3 hours and then cooled to 25° C. The reaction mixture was extracted 3 times with 250 mL of diethyl ether and the solvent removed in vacuo to yield the pure product. $^{31}$P NMR; δ (CDCl$_3$): 133.41 (s).

Preparation of 10-chlorophenoxaphosphine

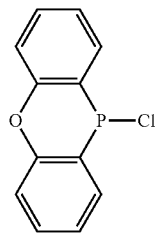 [SMILES: ClP1c2ccccc2Oc2ccccc21]

To a solution of diphenyl ether (3 g, 17.6 mmol) in THF (30 mL) was added a solution of n-BuLi (15.5 mL, 38.7 mmol, 2.5 M in hexane) at −40° C. The reaction mixture was allowed to warm to room temperature and stirred for 24 h. The reaction mixture was cooled to −78° C. and Et$_2$NPCl$_2$, (4.3 mL, 21.1 mmol) in THF (10 ml) slowly added. The reaction mixture was allowed to warm to room temperature and was stirred for another 3 h. The solvents were removed in vacuo and the yellow oil was dissolved in 50 mL of diethyl ether. Dry HCl in diethyl ether was added to the solution at room temperature and the reaction stirred under nitrogen flow for a further 15 min. The ammonium salt was removed by filtration on a celite pad. The solvent was removed in vacuo to leave the product as a yellow oil. $^{31}$P NMR; δ (CDCl$_3$): 33.86 (s).

Preparation of (dibenzophosphol-5-yl)N(i-propyl)P(2-methylphenyl)$_2$

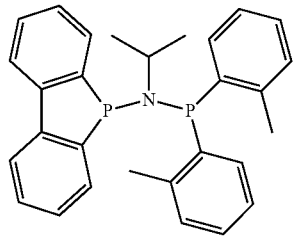 [SMILES: Cc1ccccc1P(c1ccccc1C)N(C(C)C)p1c2ccccc2c2ccccc21]

PNH formation: iso-Propylamine (0.52 mL, 6.0 mmol) and Et$_3$N (0.83 mL, 6.0 mmol) were added to the crude 5-chlorodibenzophosphole (1.1 g, 5.0 mmol) [prepared as described above] in diethyl ether (30 ml). The reaction mixture was stirred at room temperature until complete formation of the PNH intermediate as judged by $^{31}$P NMR analysis. The volatiles were removed in vacuo. Ether (50 ml) was added and the resultant mixture filtered to give the ether solution of the desired PNH product in reasonable purity [(by $^{31}$P NMR analysis]. The solvent was removed in vacuo to give the PNH compound, (dibenzophosphol-5-yl)N(i-propyl)H. $^{31}$P NMR (CDCl$_3$): δ 33.39 (s).

PNP formation: The PNH (dibenzophosphol-5-yl)N(i-propyl)H (0.58 g, 2.4 mmol) was re-dissolved in DCM (10 ml). Et$_3$N (0.68 ml, 4.9 mmol) was added, followed by incremental addition of (2-methylphenyl)$_2$phosphinechloride (0.72 g, 2.9 mmol) [prepared as described above] at room temperature. After complete conversion of the PNH (judged by $^{31}$P NMR analysis) to the PNP, the solvent was removed in vacuo from the post reaction mixture. Ether (100 ml) was added and the resultant mixture was filtered through a short activated alumina column. Filtration was repeated until a pure compound was obtained. The solvent was evaporated to give the desired PNP product. $^{31}$P NMR (CDCl$_3$): δ 47.18 (s, br), 22.84 (s, br).

Preparation of (dibenzophosphol-5-yl)N(i-butyl)P(2-methylphenyl)$_2$

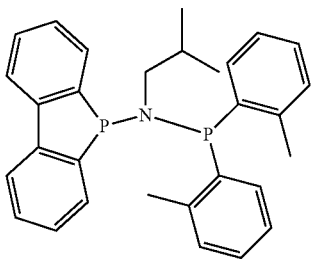 [SMILES: Cc1ccccc1P(c1ccccc1C)N(CC(C)C)p1c2ccccc2c2ccccc21]

PNH formation: (dibenzophosphol-5-yl)N(i-butyl)H was prepared as described above for (dibenzophosphol-5-yl)N(i-propyl)H except that iso-butylamine was used instead of iso-propylamine. $^{31}$P NMR (CDCl$_3$): 37.21 (s).

PNP formation: The PNP compound was prepared from the reaction of (dibenzophosphol-5-yl)N(i-butyl)H (1.0 g, 3.9 mmol), Et$_3$N (1.08 ml, 7.8 mmol), and (2-methylphenyl)$_2$phosphine-chloride (1.2 g, 4.7 mmol) following the typical procedure described for the preparation of (dibenzophosphol-5-yl)N(i-propyl)P(2-methylphenyl)$_2$ above. $^{31}$P NMR (CDCl$_3$): δ 73.41 (s), 65.58 (s).

Preparation of (dibenzophosphol-5-yl)N(i-propyl)P(2-methoxyphenyl)$_2$

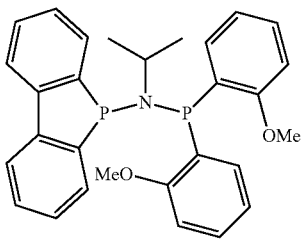 [SMILES: COc1ccccc1P(c1ccccc1OC)N(C(C)C)p1c2ccccc2c2ccccc21]

PNH formation: (dibenzophosphol-5-yl)N(i-propyl)H was prepared as described above. $^{31}$P NMR (CDCl$_3$): 33.38 (s).

PNP formation: The PNP compound was prepared from the reaction of (dibenzophosphol-5-yl)N(i-propyl)H (1.0 g, 3.9 mmol), Et$_3$N (1.08 ml, 7.8 mmol) and (2-methoxyphenyl)$_2$phosphine chloride (1.3 g, 4.7 mmol) [prepared as described above] following the typical procedure described for the preparation of (dibenzophosphol-5-yl)N(i-propyl)P(2-methylphenyl)$_2$ above. $^{31}$P NMR (CDCl$_3$): δ 48.052 (br. s), 17.19 (br. s).

Preparation of (dibenzophosphol-5-yl)N(n-butyl)P(2-methoxyphenyl)$_2$

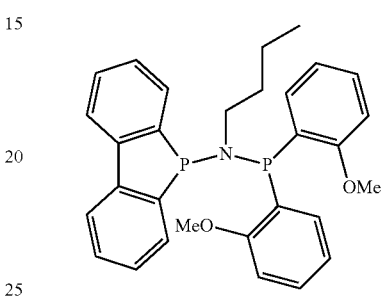

PNH formation: (dibenzophosphol-5-yl)N(n-butyl)H was prepared as described above for (dibenzophosphol-5-yl)N(i-propyl)H except that n-butylamine was used instead of iso-propylamine. $^{31}$P NMR (CDCl$_3$): 37.2 (s).

PNP formation: The PNP compound was prepared from the reaction of (dibenzophosphol-5-yl)N(n-butyl)H (1.0 g, 3.9 mmol), Et$_3$N (1.08 ml, 7.8 mmol), and (2-methoxyphenyl)$_2$phosphine-chloride (1.3 g, 4.7 mmol) [prepared as described above] following the typical procedure described for the preparation of (dibenzophosphol-5-yl)N(i-propyl)P(2-methylphenyl)$_2$ above. $^{31}$P NMR (CDCl$_3$): δ 53.8 (d, J=142.00 Hz), 48.8 (d, J=140.55 Hz).

Preparation of (dibenzophosphol-5-yl)N(i-propyl(2-fluorophenyl)$_2$

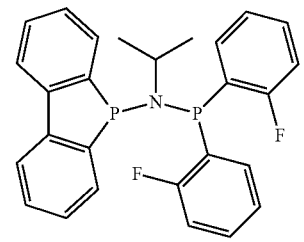 [SMILES: CC(C)N(P(c1ccccc1F)c1ccccc1F)p1c2ccccc2c2ccccc21]

PNH formation: (dibenzophosphol-5-yl)N(i-propyl)H was prepared as described above. $^{31}$P NMR (CDCl$_3$): 33.39 (s).

PNP formation: The PNP compound was prepared from the reaction of (dibenzophosphol-5-yl)N(i-propyl)H (1.5 g, 7.0 mmol), Et$_3$N (1.5 ml, 10.5 mmol), and (2-fluorophenyl)$_2$phosphine chloride (2 g, 7.7 mmol) [prepared as described above] following the typical procedure described for the preparation of (dibenzophosphol-5-yl)N(i-propyl)P(2-methylphenyl)$_2$ above. $^{31}$P NMR (CDCl$_3$): δ 49.64 (br s), 15.92 (br s).

Preparation of (dibenzophosphol-5-yl)N(n-butyl)P
(1-benzofuran-7-yl)(phenyl)

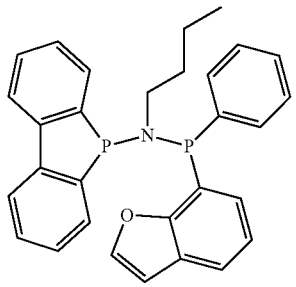 [SMILES: CCCCN(P(c1ccccc1)c1cccc2ccoc12)p1c2ccccc2c2ccccc21]

PNH formation: (dibenzophosphol-5-yl)N(n-butyl)H was prepared as described above for (dibenzophosphol-5-yl)N(i-propyl)H except that n-butylamine was used instead of iso-propylamine. $^{31}$P NMR (CDCl$_3$): 37.2 (s).

PNP formation: The PNP compound was prepared from the reaction of (dibenzophosphol-5-yl)-N(n-butyl)H (1.5 g, 5.9 mmol), Et$_3$N (1.1 ml, 8.3 mmol), and (1-benzofuran-7-yl)(phenyl)-phosphinechloride (1.8 g, 7.1 mmol) following the typical procedure described for the preparation of (dibenzophosphol-5-yl)N(i-propyl)P(2-methylphenyl)$_2$ above. $^{31}$P NMR (CDCl$_3$): δ 55.85 (d, J=93.5 Hz), 53.92 (d, J=94.2 Hz).

Preparation of (9-oxa-10-phosphaphenathren-10-yl)
N(i-propyl)P(2-methoxyphenyl)$_2$

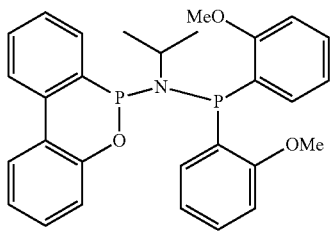 [SMILES: COc1ccccc1P(c1ccccc1OC)N(C(C)C)P1Oc2ccccc2-c2ccccc21]

PNH formation: iso-Propylamine (0.7 ml, 7.7 mmol) and Et$_3$N (1.1 ml, 7.7 mmol) were added to the crude 10-chloro-9-oxa-10-phosphaphenanthrene (1.5 g, 6.4 mmol) [prepared as described above] in diethyl ether (30 ml). The reaction mixture was stirred at room temperature until complete formation of the PNH intermediate as judged by $^{31}$P NMR analysis. The volatiles were removed in vacuo. Ether (50 ml) was added and the resultant mixture filtered to give the ether solution of the desired PNH product in reasonable purity [by $^{31}$P NMR analysis]. The solvent was removed in vacuo to give the PNH compound, (10-oxa-9-phosphaphenathren-9-yl)N(i-propyl)H. $^{31}$P NMR (CDCl$_3$): δ 75.20 (s).

PNP formation: The PNH (10-oxa-9-phosphaphenathren-9-yl)N(i-propyl)H (1.6 g, 6.4 mmol) was re-dissolved in DCM (10 ml). Et$_3$N (1.1 ml, 7.7 mmol) was added, followed by incremental addition of (2-methoxyphenyl)$_2$phosphine chloride (2.2 g, 7.7 mmol) [prepared as described above] at room temperature. After complete conversion of the PNH (judged by $^{31}$P NMR analysis) to the PNP, the solvent was removed in vacuo from the post reaction mixture. Ether (100 ml) was added and the resultant mixture was filtered through a short activated alumina column. Filtration was repeated until a pure compound was obtained. The solvent was evaporated to give the desired PNP product. $^{31}$P NMR (CDCl$_3$): δ 93.36 (s), 20.06 (5).

Preparation of (phenoxaphosphin-10-yl)N(n-butyl)P
(phenyl)$_2$

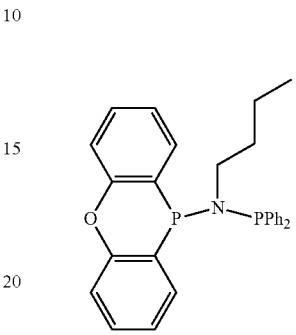

PNH formation: n-Butylamine (1.1 ml, 10.2 mmol) and Et$_3$N (1.8 ml, 12.8 mmol) were added to the crude 10-chlorophenoxaphosphine (2 g, 8.5 mmol) [prepared as described above] in diethyl ether (30 ml). The reaction mixture was stirred at room temperature until complete formation of the PNH intermediate as judged by $^{31}$P NMR analysis. The volatiles were removed in vacuo. Ether (50 ml) was added and the resultant mixture filtered to give the ether solution of the desired PNH product in reasonable purity [(by $^{31}$P NMR analysis]. The solvent was removed in vacuo to give the PNH compound, (phenoxaphosphin-10-yl)N(n-butyl)H. $^{31}$P NMR (CDCl$_3$): δ −3.44 (s).

PNP formation: The PNH (phenoxaphosphin-10-yl)N(n-butyl)H (1.5 g, 5.5 mmol) was re-dissolved in DCM (10 ml). Et$_3$N (1.2 ml, 8.3 mmol) was added, followed by incremental addition of Ph$_2$PCl (1.2 ml, 6.6 mmol) at room temperature. After complete conversion of the PNH (judged by $^{31}$P NMR analysis) to the PNP, the solvent was removed in vacuo from the post reaction mixture. Ether (100 ml) was added and the resultant mixture was filtered through a short activated alumina column. Filtration was repeated until a pure compound was obtained. The solvent was evaporated to give the desired PNP product. $^{31}$P NMR (CDCl$_3$): δ 76.32 (d, J=30.5 Hz), 50.36 (d, J=29.8 Hz).

Preparation of (phenoxaphosphin-10-yl)N(n-butyl)P
(2-fluorophenyl)$_2$

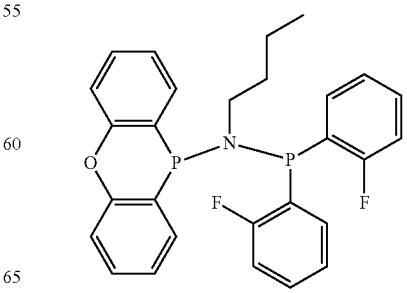

PNH formation: (phenoxaphosphin-10-yl)N(n-butyl)H was prepared as described above. ³¹P NMR (CDCl₃): δ −3.44 (5).

PNP formation: The PNP compound was prepared from the reaction of (phenoxaphosphin-10-yl)N(n-butyl)H (1.7 g, 6.4 mmol), Et₃N (1.2 ml, 8.3 mmol), and (2-fluorophenyl)₂ phosphine chloride (1.6 g, 6.4 mmol) [prepared as described above] following the typical procedure described for the preparation of (phenoxaphosphin-10-yl)N(n-butyl)P(phenyl)₂ above. ³¹P NMR (CDCl₃): δ 44.09 (dt, J=233.7 Hz and J=46.5 Hz), 15.25 (d, J=233.7 Hz).

Preparation of (phenyl)₇PN(n-butyl)P(phenyl)₂

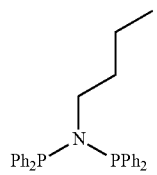

This compound was prepared from the reaction of n-butylamine (1.0 g, 13.7 mmol), Et₃N (5.54 g, 54.7 mmol), Ph₂PCl (7.59 g, 41.0 mmol), following a procedure described in Synthesis, 2007, 24, 3863. ³¹P NMR (CDCl₃): δ 62.5 (s).

Preparation of (phenyl)₂PN(n-butyl)P(2-methoxyphenyl)₂

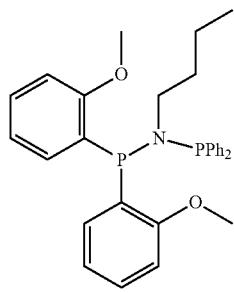

PNH formation: An ethereal solution of n-butylamine (1.5 g, 20.1 mmol) and Et₃N (2.0 g, 20.1 mmol) at ~0° C. was added to an ethereal solution of (2-methoxyphenyl)₂PCl (5.6 g, 20.1 mmol) [prepared as described above]. A white precipitate formed immediately. The reaction mixture was left to stir for 1 hr followed by filtration of the precipitate and removal of the solvent in vacuo to give (2-methoxyphenyl)₂PN(n-butyl)H. ³¹P NMR (CDCl₃): δ 26.37 (s).

PNP formation: To a DCM (3 ml) solution of (2-methoxyphenyl)₂PN(n-butyl)H (2.4 g, 8.5 mmol)) and Et₃N (1.4 ml, 10.2 mmol) was added ClPPh₂ (1.58 g, 8.5 mmol). The reaction was left to stir overnight. The solvent was then removed in vacuo and the residue re-slurried in ether (100 ml), followed by filtration of the solids and removal of the solvent in vacuo to give the desired PNP product. ³¹P NMR; δ (CDCl₃): 57.74 (br 5), 43.85 (d, J=49.89 Hz).

Preparation of (phenyl)₂PN(i-propyl)P(2-methoxyphenyl)₂

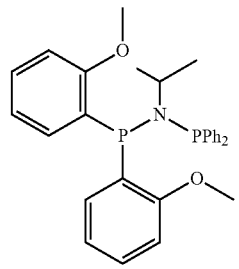

PNH formation: (2-methoxyphenyl)₂PN(i-propyl)H was prepared as described above for (2-methoxyphenyl)₂PN(n-butyl)H except that i-propyl amine was used instead of n-butyl amine. ³¹P NMR (CDCl₃): δ 19.02 (s).

PNP formation: The PNP compound was prepared from the reaction of (2-methoxyphenyl)₂PN(i-propyl)H (1.5 g, 4.9 mmol), Et₃N (1.4 ml, 9.9 mmol), and ClPPh₂ (0.9 ml, 4.9 mmol) following the typical procedure described for preparation of (phenyl)₂PN(n-butyl)P(2-methoxyphenyl)₂ above. ³¹P NMR (CDCl₃): δ 54.66 (br s), 21.79 (br, s).

Preparation of (phenyl)₂PN(i-propyl)P(2-fluorophenyl)₂

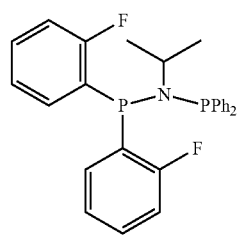

PNH formation: An ethereal solution of iso-propylamine (0.5 g, 8.46 mmol) and Et₃N (2.3 ml, 16.9 mmol) at ~0° C. was added to an ethereal solution of (2-fluorophenyl)₂PCl (1.81 g, 7.1 mmol) [prepared as described above]. A white precipitate formed immediately. The reaction mixture was left to stir for 1 hr followed by filtration of the precipitate and removal of the solvent in vacuo to give (2-fluorophenyl)₂ PN(i-propyl)H. ³¹P NMR (CDCl₃): δ 15.7 (t, J=33.4 Hz).

PNP formation: To a DCM (3 ml) solution of (2-fluorophenyl)₂PN(i-propyl)H (0.8 g, 2.9 mmol) and Et₃N (0.56 g, 5.9 mmol) was added ClPPh₂ (0.54 ml, 2.9 mmol). The reaction was left to stir overnight. The solvent was then removed in vacuo and the residue re-slurried in ether (100 ml), followed by filtration of the solids and removal of the solvent in vacuo to give the desired PNP product. ³¹P NMR (CDCl₃): δ 52.5 (br s), 22.6 (br s).

Preparation of (phenyl)$_2$PN(n-butyl)P(2-fluorophenyl)$_2$

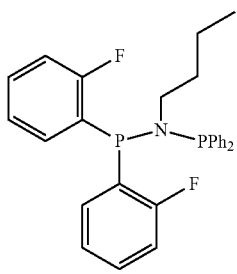

PNH formation: (2-fluorophenyl)$_2$PN(n-butyl)H was prepared as described above for (2-fluorophenyl)$_2$PN(i-propyl)H except that n-butyl amine was used instead of iso-propyl amine.

PNP formation: The PNP compound was prepared from the reaction of (2-fluorophenyl)$_2$PN(n-butyl)H (1.5 g, 4.8 mmol), Et$_3$N (1.3 ml, 9.5 mmol), and ClPPh$_2$ (0.9 ml, 4.8 mmol) following the typical procedure described for preparation of (phenyl)$_2$PN(i-propyl)P(2-fluorophenyl)$_2$ above. $^{31}$P NMR (CDCl$_3$): δ 63.2 (d, J=41.6 Hz), 39.0 (m).

Preparation of (phenyl)$_2$PN(i-propyl)P(2-methylphenyl)$_2$

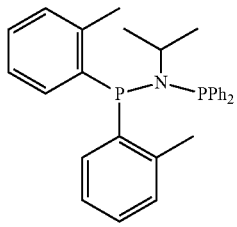

PNH formation: An ethereal solution of iso-propylamine (1.5 g, 25.4 mmol) and Et$_3$N (2.0 g, 30.5 mmol) at ~0° C. was added to an ethereal solution of (2-methylphenyl)$_2$PCl (6.3 g, 25.4 mmol) [prepared as described above]. A white precipitate formed immediately. The reaction mixture was left to stir for 1 hr followed by filtration of the precipitate and removal of the solvent in vacuo to give (2-methyl phenyl)$_2$PN(i-propyl)H.

PNP formation: To a DCM (3 ml) solution of (2-methylphenyl)$_2$PN(i-propyl)H (2.4 g, 8.5 mmol) and Et$_3$N (1.4 ml, 10.2 mmol) was added ClPPh$_2$ (1.58 g, 8.5 mmol). The reaction was left to stir overnight. The solvent was then removed in vacuo and the residue re-slurried in ether (100 ml), followed by filtration of the solids and removal of the solvent in vacuo to give the desired PNP product. $^{31}$P NMR (CDCl$_3$): δ 52.9 (s, br), 26.2 (s, br).

Preparation of (phenyl)$_2$PN(i-butyl)P(2-methylphenyl)$_2$

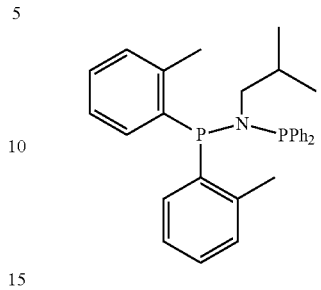

PNH formation: (2-methylphenyl)$_2$PN(i-butyl)H was prepared as described above for (2-methylphenyl)$_2$PN(i-butyl)H, except that iso-butyl amine was used instead of iso-propyl amine.

PNP formation: The PNP compound was prepared from the reaction of (2-methylphenyl)$_2$-PN(i-butyl)H (1.5 g, 4.7 mmol), Et$_3$N (0.9 ml, 6.6 mmol), and ClPPh$_2$ (0.9 ml, 4.7 mmol) following the typical procedure described for the preparation of (phenyl)$_2$PN(i-propyl)P(2-methylphenyl)$_2$ above. $^{31}$P NMR (CDCl$_3$): δ 62.5 (br s), 54.9 (br s).

Preparation of (phenyl)$_2$PN(n-Hexyl)P(1-benzofuran-7-yl)(phenyl)

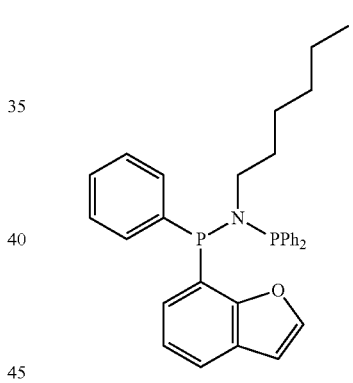

PNH formation: n-Hexylamine (0.95 mL, 7.2 mmol) and Et$_3$N (1.0 mL, 7.2 mmol) were added to the crude (1-benzofuran-7-yl)(phenyl)phosphine chloride (0.90 g, 3.6 mmol) [prepared as described above] in diethyl ether (30 ml). The reaction mixture was stirred at room temperature until complete formation of the PNH intermediate as judged by $^{31}$P NMR analysis. The volatiles were removed in vacuo. Ether (50 ml) was added and the resultant mixture filtered to give the ether solution of the desired PNH product in reasonable purity [by $^{31}$P NMR analysis]. The solvent was removed in vacuo to give the PNH compound, (1-benzofuran-7-yl)(phenyl)PN(n-Hex)H.

PNP formation: The PNH (1-benzofuran-7-yl)(phenyl)PN(n-Hex)H (0.80 g, 2.4 mmol) was re-dissolved in DCM (10 ml). Et$_3$N (0.5 g, 4.9 mmol) was added, followed by incremental addition of Ph$_2$PCl (1.1 g, 4.9 mmol) at room temperature. After complete conversion of the PNH (judged by $^{31}$P NMR analysis) to the PNP, the solvent was removed from the post reaction mixture. Ether (100 ml) was added and the resultant mixture was filtered through a short activated alumina column. Filtration was repeated until a pure compound was obtained. The solvent was evaporated to give the desired PNP product. $^{31}$P NMR (CDCl$_3$): δ 62.9 (d, J=37.6 Hz), 50.5 (d, J=37.6 Hz).

Example 1

Ethylene tetramerisation with (dibenzophosphol-5-yl)N(i-propyl)P(2-methylphenyl)$_2$ at 60° C. and 45 bar A 600 ml stainless steel reactor was heated to 120° C. for 30 minutes under vacuum, backfilled with N$_2$ and then cooled to 60° C. The reactor was charged with 2,2,4-trimethylpentane (TMP) (100 ml), and heated to 60° C. Separately, MMAO-3A (2.4 mmol Al) was added to a mixture of Cr(acac)$_3$ (2.5 μmol) and (dibenzophosphol-5-yl)N(i-propyl)P(2-methylphenyl)$_2$ (2.5 μmol) in cyclohexane (5 ml). This mixture was then transferred to the reactor. The reactor was pressurised with ethylene (45 bar), and stirred (1300 r.p.m.) with a gas entraining stirrer. The temperature in the reactor increased to 62-65° C., at which point the reactor was cooled by means of an internal cooling coil to maintain a constant temperature of 60° C. throughout the run. The reaction pressure was kept constant throughout the run by feeding ethylene on demand, and the consumption of ethylene was monitored via a flow meter. At the conclusion of the run after 34.3 minutes and 160 g total ethylene uptake (including the ethylene required to pressurise the reactor), the reactor was rapidly cooled to 5° C., and depressurised. A weighed mass of nonane was added as an internal standard, and a small sample was taken for GC-FID analysis. The polymer by-product was collected by filtration, dried overnight and weighed. The selectivity and activity were then calculated from the GC data and polymer mass. The results are shown in Table 1.

Example 2

Ethylene tetramerisation with (dibenzophosphol-5-yl)N(i-butyl)P(2-methylphenyl)$_2$ at 60° C. and 45 bar The procedure of example 1 was followed, except that the ligand (dibenzophosphol-5-yl)N(i-butyl)P(2-methylphenyl)$_2$ was used, and the reaction was terminated after 61 minutes and 160 g ethylene uptake. The results are shown in Table 1.

Example 3

Ethylene tetramerisation with (dibenzophosphol-5-yl)N(n-butyl)P(2-methoxyphenyl)$_2$ at 60° C. and 45 bar The procedure of example 1 was followed, except that the ligand (dibenzophosphol-5-yl)N(n-butyl)P(2-methoxyphenyl)$_2$ was used, and the reaction was terminated after 58 minutes and 160 g ethylene uptake. The results are shown in Table 1.

Example 4

Ethylene tetramerisation with (dibenzophosphol-5-yl)N(i-propyl)P(2-methoxyphenyl)$_2$ at 60° C. and 45 bar The procedure of example 1 was followed, except that the ligand (dibenzophosphol-5-yl)N(i-propyl)P(2-methoxyphenyl)$_2$ was used, and the reaction was terminated after 67 minutes and 160 g ethylene uptake. The results are shown in Table 1.

Example 5

Ethylene tetramerisation with (dibenzophosphol-5-yl)N(n-butyl)P(2-methoxyphenyl)$_2$ at 100° C. and 45 bar The procedure of example 1 was followed, except that the ligand (dibenzophosphol-5-yl)N(n-butyl)P(2-methoxyphenyl)$_2$ was used, 200 ml of TMP was used, the reaction temperature was maintained at 100° C. and the reaction was terminated after 76 minutes and 150 g ethylene uptake. The results are shown in Table 1.

Example 6

Ethylene tetramerisation with (dibenzophosphol-5-yl)N(i-propyl)P(2-fluorophenyl)$_2$ at 100° C. and 45 bar The procedure of example 1 was followed, except the ligand (dibenzophosphol-5-yl)N(i-propyl)P(2-fluorophenyl)$_2$ was used 200 ml of TMP was used, the reaction temperature was maintained at 100° C., and the reaction was terminated after 54 minutes and 150 g ethylene uptake. The results are shown in Table 1.

Example 7

Ethylene tetramerisation with (dibenzophosphol-5-yl)N(n-butyl)P(1-benzofuran-7-yl)(phenyl) at 100° C. and 45 bar The procedure of example 1 was followed, except that the ligand (dibenzophosphol-5-yl)N(n-butyl)P(1-benzofuran-7-yl)(phenyl) was used, 200 ml of TMP was used, the reaction temperature was maintained at 100° C., and terminated after 42 minutes and 150 g ethylene uptake. The results are shown in Table 1.

Example 8

Ethylene tetramerisation with (9-oxa-10-phosphaphenanthren-10-yl)N(i-propyl)P(2-methoxyphenyl)$_2$ at 60° C. and 45 bar The procedure of example 1 was followed, except that the ligand phosphaphenanthren-10-yl)N(i-propyl)P(2-methoxyphenyl)$_2$ was used, and the reaction was terminated after 77.4 minutes and 160 g ethylene uptake. The results are shown in Table 2.

Example 9

Ethylene tetramerisation with (phenoxaphosphin-10-yl)N(n-butyl)P(phenyl)$_2$ at 60° C. and 45 bar The procedure of example 1 was followed, except that the ligand (phenoxaphosphin-10-yl)N(n-butyl)P(phenyl)$_2$ was used, and the reaction was terminated after 92 minutes and 150 g ethylene uptake. The results are shown in Table 3.

Example 10

Ethylene tetramerisation with (phenoxaphosphin-10-yl)N(n-butyl)P(2-fluorophenyl)$_2$ at 60° C. and 45 bar The procedure of example 1 was followed, except that the ligand (phenoxaphosphin-10-yl)N(n-butyl)P(2-fluorophenyl)$_2$ was used, and the reaction was terminated after 24 minutes and 160 g ethylene uptake. The results are shown in Table 3.

Example 11

Ethylene tetramerisation with (phenoxaphosphin-10-yl)N(n-butyl)P(2-fluorophenyl)$_2$ at 100° C. and 45 bar The procedure of example 1 was followed, except the ligand (phenoxaphosphin-10-yl)N(n-butyl)(2-fluorophenyl)$_2$ was used, 200 ml of TMP was used, the reaction temperature was maintained at 100° C., and the reaction was terminated after 25 minutes and 97 g ethylene uptake. The results are shown in Table 3.

Comparative Example 1

Ethylene tetramerisation with (phenyl)PN(i-propyl)P(2-methylphenyl) at 60° C. and 45 bar The procedure of example 1 was followed, except that the ligand (phenyl)$_2$PN(i-propyl)P(2-methylphenyl)$_2$ was used, and the reaction was terminated after 18 minutes and 160 g ethylene uptake. The results are shown in Table 1.

Comparative Example 2

Ethylene tetramerisation with (phenyl)$_2$PN(i-butyl)P(2-methylphenyl)$_2$ at 60° C. and 45 bar The procedure of example 1 was followed, except that the ligand (phenyl)$_2$PN(i-butyl)P(2-methylphenyl)$_2$ was used, and the reaction was terminated after 11 minutes and 160 g ethylene uptake. The results are shown in Table 1.

Comparative Example 3

Ethylene tetramerisation with (phenyl)$_2$PN(n-butyl)P(2-methoxyphenyl)$_2$ at 60° C. and 45 bar The procedure of example 1 was followed, except that the ligand (phenyl)$_2$PN(n-butyl)P(2-methoxyphenyl)$_2$ was used, and the reaction was terminated after 78 minutes and 160 g ethylene uptake. The results are shown in Table 1.

Comparative Example 4

Ethylene tetramerisation with (phenyl)$_2$PN(i-propyl)P(2-methoxyphenyl)$_2$ at 60° C. and 45 bar The procedure of example 1 was followed, except that the ligand (phenyl)$_2$PN(i-propyl)P(2-methoxyphenyl)$_2$ was used, and the reaction was terminated after 60 minutes and 88 g ethylene uptake. The results are shown in Table 1.

Comparative Example 5

Ethylene tetramerisation with (phenyl)$_2$PN(n-butyl)P(2-methoxyphenyl), at 10° C. and 45 bar The procedure of example 1 was followed, except the ligand (phenyl)$_2$PN(n-butyl)P(2-methoxyphenyl)$_2$ was used, 200 ml of TMP was used, the reaction temperature was maintained at 100° C., and the reaction was terminated after 27.1 minutes and 153 g ethylene uptake. The results are shown in Table 1.

Comparative Example 6

Ethylene tetramerisation with (phenyl)$_2$PN(i-propyl)P(2-fluorophenyl), at 100° C. and 45 bar The procedure of example 1 was followed, except the ligand (phenyl)$_2$PN(i-propyl)P(2-fluorophenyl)$_2$ was used, 200 ml of TMP was used, the reaction temperature was maintained at 100° C., and the reaction was terminated after 15 minutes and 150 g ethylene uptake. The results are shown in Table 1.

Comparative Example 7

Ethylene tetramerisation with (phenyl)$_2$PN(n-butyl)P(1-benzofuran-7-yl)(phenyl) at 100° C. and 45 bar The procedure of example 1 was followed, except the ligand (phenyl)$_2$PN(n-butyl)P(1-benzofuran-7-yl)(phenyl) was used, 200 ml of TMP was used, the reaction temperature was maintained at 100° C., and the reaction was terminated after 11 minutes and 150 g ethylene uptake. The results are shown in Table 1.

Comparative Example 8

Ethylene tetramerisation with (phenyl)$_2$PN(n-butyl)P(phenyl)$_2$ at 60° C. and 45 bar The procedure of example 1 was followed, except that the ligand (phenyl)$_2$PN(n-butyl)P(2-phenyl)$_2$ was used, and the reaction was terminated after 46 minutes and 160 g ethylene uptake. The results are shown in Table 3.

Comparative Example 9

Ethylene tetramerisation with (phenyl)$_2$PN(n-butyl)P(2-fluorophenyl)$_2$ at 60° C. and 45 bar The procedure of example 1 was followed, except that the ligand (phenyl)$_2$PN(n-butyl)P(2-fluorophenylphenyl)$_2$ was used, and the reaction was terminated after 21.5 minutes and 160 g ethylene uptake. The results are shown in Table 3.

Comparative Example 10

Ethylene tetramerisation with (phenyl)$_2$PN(n-butyl)P(2-fluorophenylphenyl)$_2$ at 100° C. and 45 bar The procedure of example 1 was followed, except that ligand (phenyl)$_2$PN(n-butyl)P(2-fluorophenylphenyl)$_2$ was used, 200 ml of TMP was used, the reaction temperature was maintained at 100° C., and the reaction was terminated after only 45 minutes and 200 g ethylene uptake (including the ethylene required to pressurise the reactor). The results are shown in Table 3.

TABLE 1

| Example | Ligand | Temp. (° C.), Press. (bar) | Activity (×10⁶ g/gCr/h) | Liquid Product selectivity (wt % of oligomer products) | | | | | 1-octene:1-hexene ratio | Total product selectivity (wt %) Polymer % |
| --- | --- | --- | --- | --- | --- | --- | --- | --- | --- | --- |
| | | | | 1-hexene % | $C_6$ cyclics % | 1-octene % | 1-hexene + 1-octene % | $C_{10}$-$_{30}$ % | | |
| 1 | (dibenzophosphol-5-yl)N(i-propyl)P(2-MePh)$_2$ | 60, 45 | 1.65 | 15.6 | 2.3 | 68.1 | 83.6 | 13.0 | 4.40 | 1.68 |
| Comp 1 | Ph$_2$PN(i-propyl)P(2-MePh)$_2$ | 60, 45 | 2.70 | 35.9 | 1.4 | 54.8 | 90.9 | 7.4 | 1.52 | 1.1 |
| 2 | (dibenzophosphol-5-yl)N(i-butyl)P(2-MePh)$_2$ | 60, 45 | 1.00 | 10.8 | 3.5 | 65.9 | 76.6 | 17.9 | 6.08 | 13.06 |
| Comp 2 | Ph$_2$PN(i-butyl)P(2-MePh)$_2$ | 60, 45 | 5.03 | 30.0 | 3.4 | 61.0 | 88.0 | 8.3 | 2.26 | 0.49 |
| 3 | (dibenzophosphol-5-yl)N(n-butyl)P(2-OMePh)$_2$ | 60, 45 | 0.57 | 22.3 | 1.2 | 59.1 | 81.5 | 13.0 | 2.65 | 3.48 |
| Comp 3 | Ph$_2$PN(n-butyl)P(2-OMePh)$_2$ | 60, 45 | 0.73 | 41.8 | 2.1 | 40.4 | 82.3 | 12.6 | 0.96 | 1.65 |
| 4 | (dibenzophosphol-5-yl)PN(i-propyl)P(2-OMePh)$_2$ | 60, 45 | 0.56 | 34.2 | 0.6 | 53.0 | 87.2 | 10.2 | 1.55 | 1.16 |
| Comp 4 | Ph$_2$PN(i-propyl)P(2-OMePh)$_2$ | 60, 45 | 0.31 | 53.5 | 1.0 | 31.5 | 85.0 | 12.6 | 0.59 | 7.90 |
| 5 | (dibenzophosphol-5-yl)PN(n-butyl)P(2-OMePh)$_2$ | 100, 45 | 0.63 | 59.5 | 1.2 | 31.9 | 91.4 | 6.2 | 0.54 | 1.00 |
| Comp 5 | Ph$_2$PN(n-butyl)P(2-OMePh)$_2$ | 100, 45 | 1.72 | 75.1 | 0.8 | 15.6 | 90.8 | 6.7 | 0.21 | 0.71 |
| 6 | (dibenzophosphol-5-yl)N(i-propyl)P(2-FPh)$_2$ | 100, 45 | 0.88 | 26.5 | 2.7 | 56.3 | 82.7 | 12.9 | 2.13 | 5.1 |
| Comp 6 | Ph$_2$PN(i-propyl)P(2-FPh)$_2$ | 100, 45 | 3.72 | 47.1 | 1.1 | 33.8 | 81.0 | 17.1 | 0.72 | 1.41 |
| 7 | (dibenzophosphol-5-yl)N(n-butyl)P(1-benzofuran-7-yl)(phenyl) | 100, 45 | 1.11 | 43.9 | 1.9 | 44.9 | 88.8 | 7.4 | 1.02 | 1.51 |
| Comp 7 | (phenyl)$_2$PN(n-hexyl)P(1-benzofuran-7-yl)(phenyl) | 100, 45 | 2.29 | 56.0 | 3.0 | 33.3 | 89.3 | 6.7 | 0.59 | 0.63 |

TABLE 2

| Example | Ligand | Temp. (° C.), Press. (bar) | Activity (×10⁶ g/gCr/h) | Liquid Product selectivity (wt % of oligomer products) | | | | | 1-octene:1-hexene ratio | Total product selectivity (wt %) Polymer % |
| --- | --- | --- | --- | --- | --- | --- | --- | --- | --- | --- |
| | | | | 1-hexene % | $C_6$ cyclics % | 1-octene % | 1-hexene + 1-octene % | $C_{10}$-$_{30}$ % | | |
| 8 | (9-oxa-10-phospha-phenanthren-10-yl)N(i-propyl)P(2-OMePh)$_2$ | 60, 45 | 0.60 | 39.6 | 0.5 | 49.6 | 89.3 | 9.1 | 1.3 | 2.61 |
| Comp 4 | Ph$_2$PN(i-propyl)P(2-OMePh)$_2$ | 60, 45 | 0.31 | 53.5 | 1.0 | 31.5 | 85.0 | 12.6 | 0.59 | 7.90 |

TABLE 3

| Example | Ligand | Temp. (° C.), Press. (bar) | Activity (×10⁶ g/gCr/h) | Liquid Product selectivity (wt % of oligomer products) | | | | | 1-octene:1-hexene ratio | Total product selectivity (wt %) Polymer % |
| --- | --- | --- | --- | --- | --- | --- | --- | --- | --- | --- |
| | | | | 1-hexene % | $C_6$ cyclics % | 1-octene % | 1-hexene + 1-octene % | $C_{10}$-$_{30}$ % | | |
| 9 | (phenoxaphosphin-10-yl)N(n-butyl)PPh$_2$ | 60, 45 | 0.43 | 11.0 | 4.7 | 66.7 | 77.6 | 14.8 | 6.05 | 1.58 |
| Comp 8 | Ph$_2$PN(n-butyl)PPh$_2$ | 60, 45 | 1.23 | 6.7 | 9.2 | 60.8 | 67.5 | 19.3 | 9.07 | 1.69 |
| 10 | (phenoxaphosphin-10-yl)N(n-butyl)P(2-FPh)$_2$ | 60, 45 | 2.32 | 10.0 | 2.4 | 66.8 | 76.9 | 19.5 | 6.7 | 4.85 |

TABLE 3-continued

| Example | Ligand | Temp. (° C.), Press. (bar) | Activity (×10⁶ g/gCr/h) | Liquid Product selectivity (wt % of oligomer products) | | | | | | Total product selectivity (wt %) Polymer % |
|---|---|---|---|---|---|---|---|---|---|---|
| | | | | 1-hexene % | $C_6$ cyclics % | 1-octene % | 1-hexene + 1-octene % | $C_{10-30}$ % | 1-octene:1-hexene ratio | |
| Comp 9 | Ph₂PN(n-butyl)P(2-FPh)₂ | 60, 45 | 3.07 | 8.3 | 4.3 | 56.0 | 64.3 | 25.8 | 6.8 | 4.61 |
| 11 | (phenoxaphosphin-10-yl)N(n-butyl)P(2-FPh)₂ | 100, 45 | 1.28 | 41.6 | 2.0 | 48.0 | 89.5 | 7.5 | 1.11 | 6.46 |
| Comp 10 | Ph₂PN(n-butyl)P(2-FPh)₂ | 100, 45 | 1.37 | 34.7 | 3.8 | 46.8 | 81.5 | 13.4 | 1.35 | 3.98 |

The invention claimed is:

1. A process for the tetramerisation of ethylene, the process including contacting ethylene with a catalyst under ethylene oligomerisation conditions, said catalyst comprising:
   i) a source of chromium;
   ii) a ligating compound of the formula $(R^1)_m AXY$ wherein A is selected from the group consisting of nitrogen, phosphorus, and oxygen;
   X is a linking group between A and Y;
   m is independently 1 or 2;
   $R^1$ is a hydrogen, a hydrocarbyl group, an organoheteryl group or a heterohydrocarbyl group with each $R^1$ being the same or being different where m is 2; and
   Y is an optionally substituted group that can be represented as

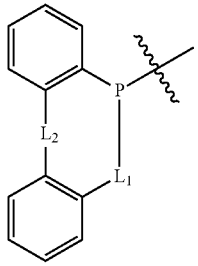

such that P is a phosphorous atom and bonds to X; and
   $L_1$ and $L_2$ are linkers selected from the group comprising a covalent bond and an optionally substituted single atom bonded to both of the linked carbon or phosphorous atoms; and
   iii) optionally a catalyst activator or combination of catalyst activators.

2. The process as claimed in claim 1, wherein A is selected from the group consisting of nitrogen and phosphorous.

3. The process as claimed in claim 1, wherein $R^1$ is a hydrocarbyl group, an organoheteryl group or a heterohydrocarbyl group.

4. The process as claimed in claim 1, wherein $R^1$ is an aromatic, including a heteroaromatic, group directly bonded to A.

5. The process as claimed in claim 1, wherein $R^1$ is an optionally substituted phenyl group.

6. A process for the tetramerisation of ethylene, the process including contacting ethylene with a catalyst under ethylene oligomerisation conditions, said catalyst comprising:
   a source of chromium;

ii) a ligating compound of the formula $R^1R^2PXY$ wherein P is a phosphorous atom;
   X is a linking group between P and Y;
   $R^1$ and $R^2$ are independently a hydrocarbyl group, an organoheteryl group or a heterohydrocarbyl group; and
   Y is an optionally substituted group that can be represented as

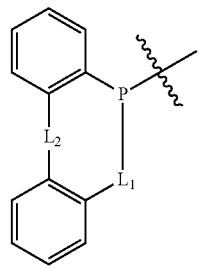

such that P is a phosphorous atom which bonds to X; and
   $L_1$ and $L_2$ are linkers selected from the group comprising a covalent bond and an optionally substituted single atom bonded to both of the linked carbon or phosphorous atoms; and
   iii) optionally a catalyst activator or combination of catalyst activators.

7. The process as claimed in claim 6, wherein $R^1$ and $R^2$ are independently a hydrocarbyl group or a heterohydrocarbyl group.

8. The process as claimed in claim 6, wherein both $R^1$ and $R^2$ are aromatic, including heteroaromatic, groups directly bonded to P.

9. The process as claimed in claim 6, wherein both $R^1$ and $R^2$ are optionally substituted phenyl groups.

10. The process as claimed in claim 6, wherein $L_1$ and $L_2$ are selected from the group comprising a covalent bond, a heteroatom, a substituted heteroatom, —C(=O)—, —CR³R⁴—, where R³ and R⁴ are independently a hydrogen, a hydrocarbyl group, a heterohydrocarbyl group or an organoheteryl group.

11. The process as claimed in claim 6, wherein $L_1$ and $L_2$ can be selected from the group comprising a covalent bond, —O—, —S—, —NR₃—, —P(=O)R³—, —P(=Se)R³—, —P(=S)R³— —SiR³R⁴—, —CR³R⁴—, —C(=O)— where R³ and R⁴ are independently a hydrogen, a hydrocarbyl group, a heterohydrocarbyl group or an organoheteryl group.

12. The process as claimed in claim 6, wherein $L_1$ and $L_2$ are either a covalent bond or —O—.

13. The process as claimed in claim 6, wherein both of $L_1$ and $L_2$ are covalent bonds.

14. The process as claimed in claim 6, wherein Y is optionally substituted at one or more of the aromatic ring positions with groups other than hydrogen including hydrocarbyl groups, heterohydrocarbyl or organoheteryl groups or halogen atom substituents.

15. A process as claimed in claim 6 wherein X is a hydrocarbylene, —N($R^5$)—, —N($R^5$)—N($R^6$)—, =C($R^7$)—N($R^5$)—, —N($R^5$)—C($R^7$)($R^8$)—, N($R^5$)—$X^1$—N($R^6$) where $R^3$ and $R^6$ are independently a hydrocarbyl group, an organoheteryl group or a heterohydrocarbyl group, $R^7$ and $R^8$ are independently a hydrogen, a hydrocarbyl group, an organoheteryl group or a heterohydrocarbyl group, and $X^1$ is a hydrocarbylene group.

16. The process as claimed in claim 1, wherein $L_1$ and $L_2$ are selected from the group comprising a covalent bond, a heteroatom, a substituted heteroatom, —C(=O)—, —$CR^3R^4$—, where $R^3$ and $R^4$ are independently a hydrogen, a hydrocarbyl group, a heterohydrocarbyl group or an organoheteryl group.

17. The process as claimed in claim 1, wherein $L_1$ and $L_2$ can be selected from the group comprising a covalent bond, —O—, —S—, —$NR_3$—, —P(=O)$R^3$—, —P(=Se)$R^3$—, —P(=S)$R^3$— —Si$R^3R^4$—, —$CR^3R^4$—, —C(=O)— where $R^3$ and $R^4$ are independently a hydrogen, a hydrocarbyl group, a heterohydrocarbyl group or an organoheteryl group.

18. The process as claimed in claim 1, wherein $L_1$ and $L_2$ are either a covalent bond or —O—.

19. The process as claimed in claim 1 wherein both of $L_1$ and $L_2$ are covalent bonds.

20. The process as claimed in claim 1, wherein Y is optionally substituted at one or more of the aromatic ring positions with groups other than hydrogen including hydrocarbyl groups, heterohydrocarbyl or organoheteryl groups or halogen atom substituents.

21. A process as claimed in claim 1 wherein X is a hydrocarbylene, —N($R^5$)—, —N($R^5$)—N($R^6$)—, =C($R^7$)—N($R^5$)—, —N($R^5$)—C($R^7$)($R^8$)—, N($R^5$)—$X^1$—N($R^6$) where $R^5$ and $R^6$ are independently a hydrocarbyl group, an organoheteryl group or a heterohydrocarbyl group, $R^7$ and $R^8$ are independently a hydrogen, a hydrocarbyl group, an organoheteryl group or a heterohydrocarbyl group, and $X^1$ is a hydrocarbylene group.

* * * * *